(12) United States Patent
Wakamatsu

(10) Patent No.: US 10,596,361 B2
(45) Date of Patent: *Mar. 24, 2020

(54) TRANSDERMAL ABSORPTION SHEET AND METHOD OF PRODUCING THE SAME

(71) Applicant: FUJIFILM Corporation, Tokyo (JP)

(72) Inventor: Satoshi Wakamatsu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 222 days.

This patent is subject to a terminal disclaimer.

(21) Appl. No.: 15/694,409

(22) Filed: Sep. 1, 2017

(65) Prior Publication Data

US 2017/0361080 A1 Dec. 21, 2017

Related U.S. Application Data

(63) Continuation of application No. PCT/JP2016/056002, filed on Feb. 29, 2016.

(30) Foreign Application Priority Data

Mar. 3, 2015 (JP) .................. 2015-041385

(51) Int. Cl.
*A61M 37/00* (2006.01)
*B81B 1/00* (2006.01)
(Continued)

(52) U.S. Cl.
CPC ........ *A61M 37/0015* (2013.01); *A61M 37/00* (2013.01); *B29C 39/026* (2013.01);
(Continued)

(58) Field of Classification Search
CPC .. A61M 2037/0023; A61M 2037/0046; A61M 2037/0053; A61M 37/00; A61M 37/0015
See application file for complete search history.

(56) References Cited

U.S. PATENT DOCUMENTS 9,968,766 B2 * 5/2018 Wakamatsu .......... A61M 37/00
2003/0009113 A1 * 1/2003 Olson ................ A61B 5/14532
600/573
(Continued)

FOREIGN PATENT DOCUMENTS

CN 102695543 A 9/2012
DE 102010001667 A1 8/2011
(Continued)

OTHER PUBLICATIONS

Extended European Search Report, dated Feb. 5, 2018, for corresponding European Application No. 16758867.2.
(Continued)

*Primary Examiner* — Ernst V Arnold
(74) *Attorney, Agent, or Firm* — Birch, Stewart, Kolasch & Birch, LLP

(57) ABSTRACT

Provided are a transdermal absorption sheet capable of achieving control of the dissolution rate and suppression of diffusion of a drug, and a method of producing the same. A transdermal absorption sheet includes a sheet portion, and a plurality of needle-like protruding portions formed by a plurality of frustum portions arranged on the sheet portion and needle portions arranged on the frustum portions, in which at least one of the needle-like protruding portions has a cavity portion extending from the sheet portion to the frustum portion.

10 Claims, 21 Drawing Sheets

(51) Int. Cl.
  *B81B 7/04* (2006.01)
  *B81C 1/00* (2006.01)
  *B29C 39/02* (2006.01)
  *B29C 39/26* (2006.01)
  *B29K 105/00* (2006.01)
  *B29L 31/00* (2006.01)

(52) U.S. Cl.
  CPC ............... *B29C 39/26* (2013.01); *B81B 1/00* (2013.01); *B81B 1/008* (2013.01); *B81B 7/04* (2013.01); *B81C 1/00* (2013.01); *B81C 1/00111* (2013.01); *A61M 2037/0023* (2013.01); *A61M 2037/0046* (2013.01); *A61M 2037/0053* (2013.01); *B29K 2105/0035* (2013.01); *B29K 2105/0073* (2013.01); *B29K 2883/00* (2013.01); *B29L 2031/7544* (2013.01); *B81B 2201/055* (2013.01)

(56) References Cited

U.S. PATENT DOCUMENTS

| | | |
|---|---|---|
| 2006/0030812 A1 | 2/2006 | Golubovic-Liakopoulos et al. |
| 2008/0200883 A1 | 8/2008 | Tomono |
| 2008/0269685 A1 | 10/2008 | Singh et al. |
| 2011/0192562 A1 | 8/2011 | Motoi et al. |
| 2012/0078189 A1 | 3/2012 | Ogawa et al. |
| 2012/0184916 A1 | 7/2012 | Kobayashi et al. |
| 2014/0272101 A1 | 9/2014 | Chen et al. |

FOREIGN PATENT DOCUMENTS

| | | |
|---|---|---|
| EP | 2462978 A1 | 6/2012 |
| JP | 2008-6178 A | 1/2008 |
| JP | 2009-233808 A | 10/2009 |
| JP | 2010-142473 A | 7/2010 |
| JP | 2010-233674 A | 10/2010 |
| JP | 2011-78617 A | 4/2011 |
| JP | 2011-206178 A | 10/2011 |
| JP | 2013-153866 A | 8/2013 |
| JP | 2013-158601 A | 8/2013 |
| JP | 2015-16362 A | 1/2015 |
| JP | 5663792 B2 | 2/2015 |
| KR | 10-0612891 B1 | 8/2006 |
| WO | WO 2006/080508 A1 | 8/2006 |
| WO | WO 2008/020633 A1 | 2/2008 |
| WO | WO 2008/130587 A2 | 10/2008 |
| WO | WO 2009/014805 A2 | 1/2009 |
| WO | WO 2009/079712 A1 | 7/2009 |
| WO | WO 2011/016230 A1 | 2/2011 |
| WO | WO 2015/009530 A1 | 1/2015 |

OTHER PUBLICATIONS

Extended European Search Report, dated Jan. 30, 2018, for European Application No. 16758868.0.
Japanese Office Action, dated Jan. 22, 2018, for Application No. 2015-041386, with an English machine translation.
Japanese Decision to Grant a Patent for corresponding Japanese Application No. 2015-041385, dated Mar. 20, 2018, with machine translation.
Japanese Notification of Reasons for Refusal and English translation for Application No. 2015-041386, dated Aug. 23, 2018.
International Preliminary Report on Patentability and English translation of Written Opinion of the International Searching Authority issued in PCT/JP2016/056002, dated Sep. 5, 2017 (Forms PCT/IB/373 and PCT/ISA/237).
International Preliminary Report on Patentability and English translation of Written Opinion of the International Searching Authority issued in PCT/JP2016/056003, dated Sep. 5, 2017 (Forms PCT/IB/373 and PCT/ISA/237).
International Search Report issued in PCT/JP2016/056003, dated May 31, 2016 (Form PCT/ISA/210).
International Search Report, issued in PCT/JP2016/056002, dated May 24, 2016 (Form PCT/ISA/210).
Japanese Office Action dated Sep. 27, 2017, issued in Japanese Patent Application JP 2015-041385.
Author Unknown, "Diameter", URL: https://www.macmilliandictionary.com/dictionary/american/diameter; 2019, pp. 1-2 (2 pages).
Author Unknown, "Facing", URL: https://www.merriam-webster.com/dictionary/facing; 2019, 1 page.
Extended European Search Report, dated May 22, 2017, for European Application No. 15792241.0.
International Search Report (Form PCT/ISA/210) dated Jul. 7, 2015, for International Application No. PCT/JP2015/060454, with an English translation.
Kivi, "Air Embolism", URL: https://www.healthline.com/health/air-embolism, Sep. 2015, 12 pages.
U.S. Office Action, dated Aug. 28, 2019, for U.S. Appl. No. 15/694,423.
Written Opinion of the International Searching Authority(Forms PCT/ISA/237), dated Jul. 7, 2015, for International Application No. PCT/JP2015/060454.
U.S. Office Action dated Jan. 2, 2020, for U.S. Appl. No. 15/694,423.
European Office Communication for European Application No. 16758868.0, dated Nov. 20, 2019.

* cited by examiner

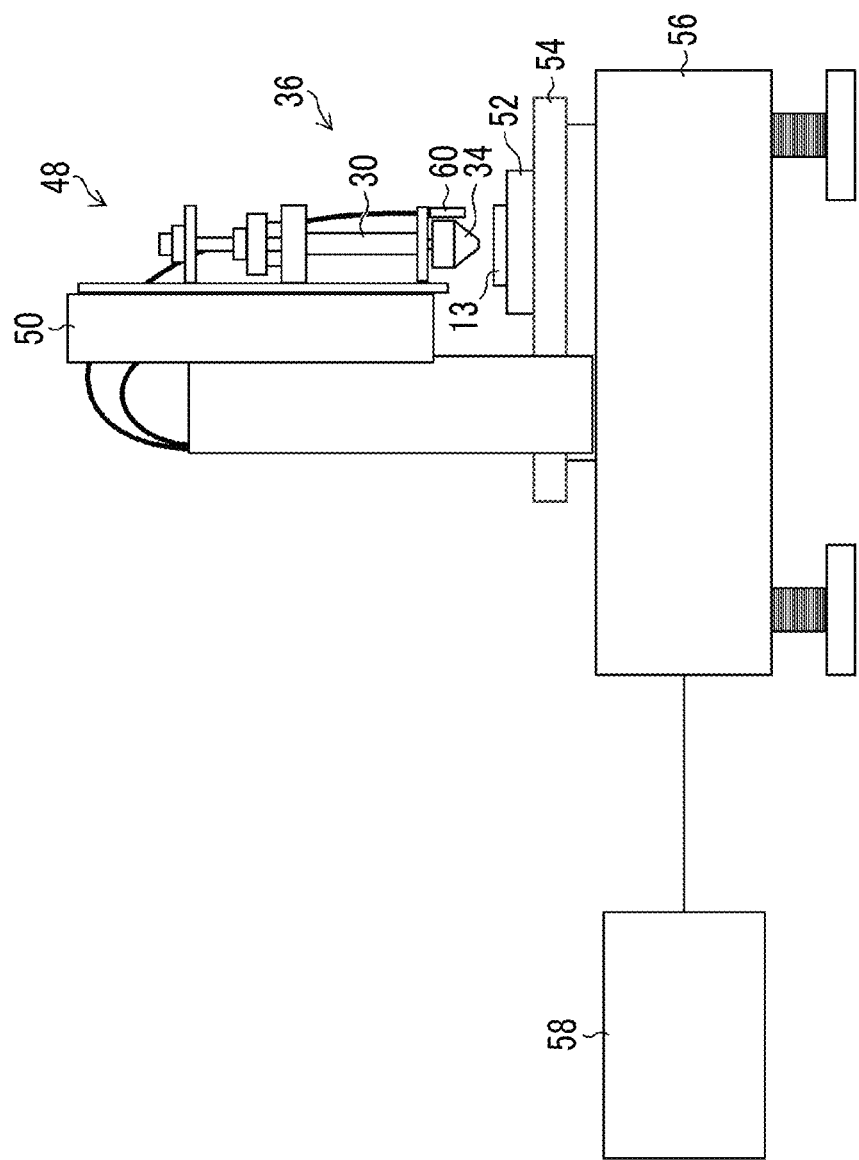

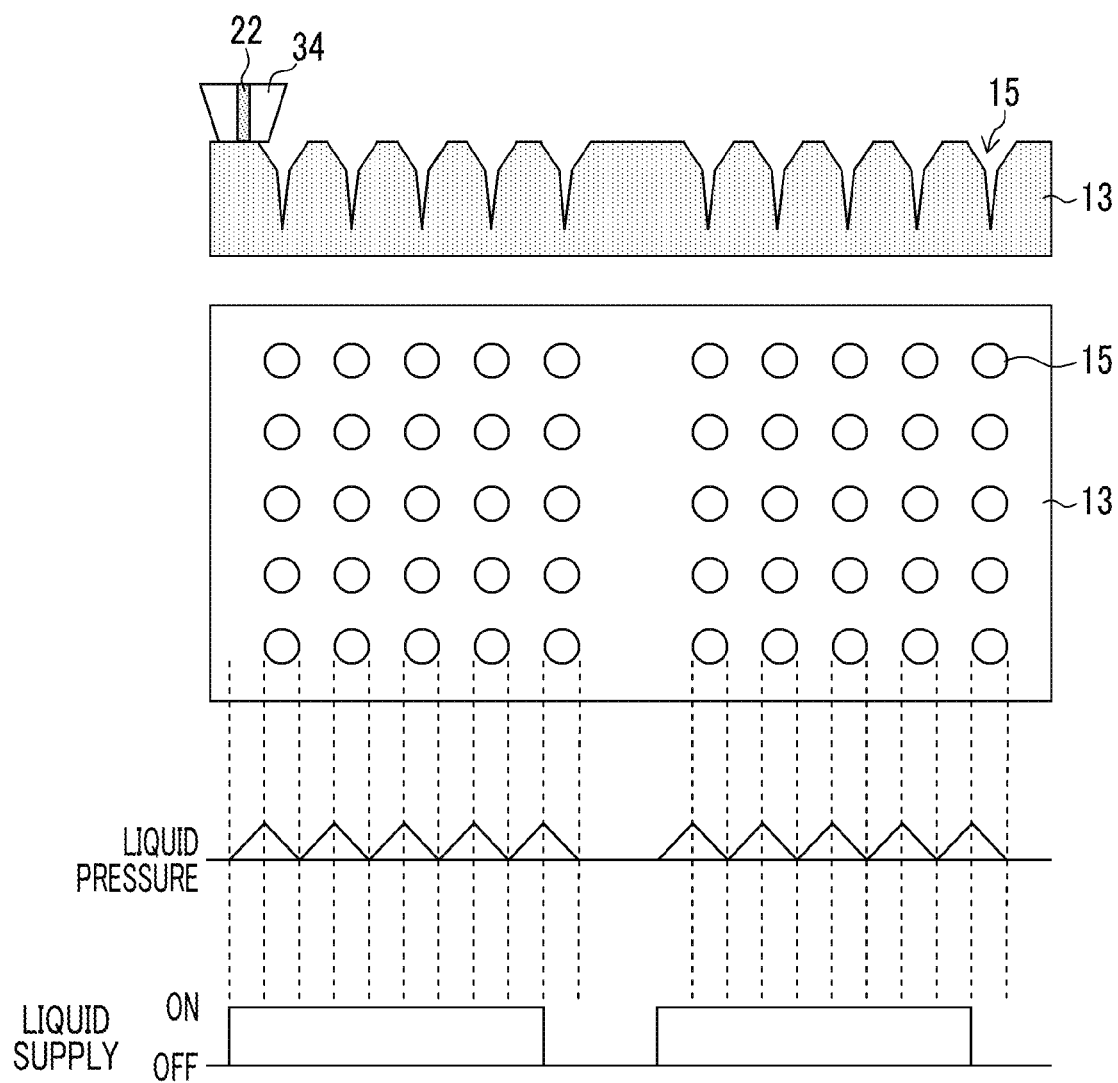

TRANSDERMAL ABSORPTION SHEET AND METHOD OF PRODUCING THE SAME

CROSS-REFERENCE TO RELATED APPLICATIONS

This application is a Continuation of PCT International Application No. PCT/JP2016/056002 filed on Feb. 29, 2016, which claims priority under 35 U.S.C. § 119(a) to Japanese Patent Application No. 2015-041385 filed on Mar. 3, 2015. Each of the above applications is hereby expressly incorporated by reference, in their entirety, into the present application.

BACKGROUND OF THE INVENTION

1. Field of the Invention

The present invention relates to a transdermal absorption sheet and a method of producing the same.

2. Description of the Related Art

In recent years, a transdermal absorption sheet having a plurality of needle-like protruding portions (also referred to as microneedles) containing a drug has been used to deliver a drug into a skin. In general, a drug in needle-like protruding portions is delivered into a skin by attaching a transdermal absorption sheet to a skin and inserting the needle-like protruding portions into the skin.

Various proposals on such a transdermal absorption sheet have been made to deliver a drug into a skin. For example, WO2006/080508A discloses that in order to administer an exact amount of a drug, which is a target substance, a constriction or split line is provided on a part of the surface of a transdermal absorption preparation having a needle-like shape so that the needle-like shape is cut along the constriction or split line after the needle-like portion is inserted into a skin.

In addition, JP2009-233808A discloses a polymer sheet having a hollow needle-like protruding portion containing a drug and a polymer sheet having a needle-like protruding portion of which the hollow portion is filled with a drug.

SUMMARY OF THE INVENTION

In WO2006/080508A, after the needle-like portion is inserted into the skin, only the part of the needle-like portion below the constriction or the split line is inserted into the skin. However, in the case in which the drug, which is a target substance, diffuses in the needle-like portion at the time of production, the drug which is not administered into the skin also remains in the transdermal absorption preparation other than the needle-like portion. Since the drug remaining in the transdermal absorption preparation is not delivered into the skin, there is a concern of wasting the drug.

In addition, in JP2009-233808A, since the drug is contained in the hollow needle-like protruding portion or the drug is contained in the hollow portion, the drug is not administered into the skin and remains in the needle-like protruding portion in some cases. Therefore, there is a concern of wasting the drug that is not delivered into the skin.

On the other hand, there is a demand for suppressing diffusion of a drug solution on the base solution side in the transdermal absorption sheet. There is also a demand for controlling the delivery speed of the drug into the skin, that is, the dissolution rate of the needle-like protruding portion containing a drug in the skin. Particularly, since it is necessary to hold the needle-like protruding portion in a state in which the needle is stuck after puncture until the drug diffuses into the skin, the holding time becomes longer in the case in which the dissolution rate is slow, which leads to poor convenience.

The present invention has been made in consideration of such circumstances, and an object thereof is to provide a transdermal absorption sheet capable of achieving control of the dissolution rate and suppression of diffusion of a drug, and a method of producing the same.

According to an aspect of the present invention, there is provided a transdermal absorption sheet comprising: a sheet-like sheet portion; and a plurality of needle-like protruding portions which are arranged on the sheet portion and formed of frustum portions and needle portions, and in each of which a wide bottom surface of the frustum portion is connected to the sheet portion and a narrow bottom surface of the frustum portion is connected to a wide bottom surface of the needle portion, in which each of the plurality of needle portions includes a first layer containing a drug and a second layer not containing a drug, and at least one of the plurality of needle-like protruding portions has a cavity portion extending from the sheet portion to the frustum portion.

The present inventors have conducted intensive investigations on a transdermal absorption sheet capable of achieving control of the dissolution rate and suppression of diffusion of a drug, and a method of producing the same. As a result, the present inventors have found that by providing a cavity portion in at least one of a plurality of needle-like protruding portions, a barrier for drug diffusion is obtained and the dissolution rate is improved, and thus accomplished the present invention.

It is preferable that at least one of the plurality of needle-like protruding portions has a cavity portion extending from the sheet portion to the needle portion through the frustum portion.

It is preferable that the cavity portion is entirely or partially formed in a dome shape.

It is preferable that a radius of curvature that defines the dome shape is 10 µm or more.

It is preferable that a thickness of the thinnest part of the needle-like protruding portion having the cavity portion is equal to or less than a thickness of the sheet portion.

It is preferable that the thickness of the thinnest part is in a range of 100 to 500 µm.

It is preferable that the cavity portion remains in the second layer.

It is preferable that the drug is at least one of peptide, protein, nucleic acid, polysaccharide, a vaccine, a medical compound, or a cosmetic component.

According to another aspect of the present invention, there is provided a method of producing a transdermal absorption sheet comprising, in this order: a drug solution filling step of filling needle-like recessed portions of a mold having the needle-like recessed portions arranged two-dimensionally with a drug solution which is a polymer solution containing a drug; a drug solution drying step of drying the drug solution filling the needle-like recessed portions to form a first layer containing a drug; a base solution filling step of filling the needle-like recessed portions with a base solution that is a polymer solution not containing a drug on the first layer; a base solution drying step of drying the base solution to form a second layer not containing a drug on the first layer and forming needle-like portions formed of frustum portions and needle portions and a sheet portion; and a peeling-off step of peeling off the sheet portion and the needle-like protruding portions from the mold, in which in the base solution drying step, a cavity portion extending from the sheet portion to the frustum portion or a cavity portion extending from the sheet portion to the needle portion through the frustum portion is formed in the needle-like protruding portion by drying and reducing the base solution.

It is preferable that the base solution drying step includes drying the base solution while cooling the mold.

It is preferable that a cooling temperature for cooling the mold is in a range of 1° C. to 20° C.

According to the transdermal absorption sheet and the method of producing a transdermal absorption sheet of the present invention, it is possible to control the dissolution rate and suppress diffusion of a drug.

BRIEF DESCRIPTION OF THE DRAWINGS

FIG. 18 is a schematic configuration view showing a drug solution filling apparatus.

FIG. 19 is an illustration showing a relationship between the liquid pressure in the nozzle and the supply of a drug-containing solution.

DESCRIPTION OF THE PREFERRED EMBODIMENTS

Figure 1:
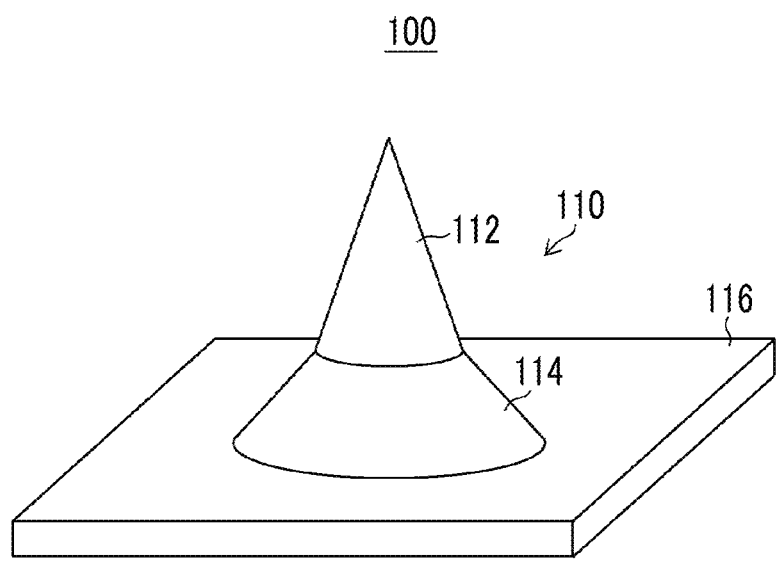
FIG. 1 is a partially enlarged view showing a transdermal absorption sheet having a needle-like protruding portion.

Hereinafter, preferred embodiments of the present invention will be described with reference to the accompanying drawings. The present invention will be described using the following preferred embodiments. Modifications can be made by many methods without departing from the scope of the present invention, and embodiments other than the embodiments can be used. Accordingly, all of the modifications within the scope of the present invention are included in the claims.

In the drawings, components designated by the same reference numeral are similar components having similar functions. Furthermore, in the present specification, in the case in which a numerical range is described using "to", numerical values for an upper limit and a lower limit illustrated with "to" are also included in the numerical range.

Figure 2:
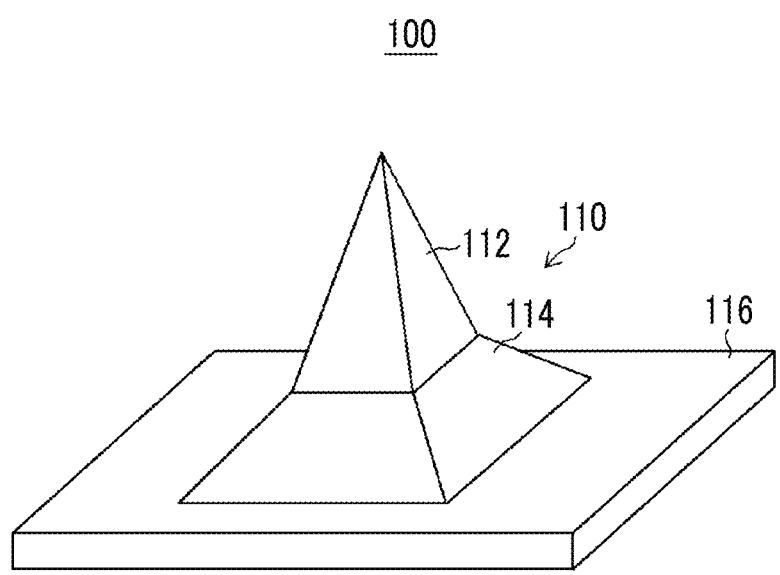
FIG. 2 is a partially enlarged view showing a transdermal absorption sheet having a needle-like protruding portion of another shape.

A transdermal absorption sheet produced in the embodiment will be described. FIGS. 1 and 2 each show a needle-like protruding portion 110 (also referred to as a microneedle) that is a partially enlarged view of a transdermal absorption sheet 100.

The transdermal absorption sheet 100 delivers a drug into the skin by being attached to the skin. As shown in FIG. 1, the transdermal absorption sheet 100 has a tapered-shaped needle portion 112, a frustum portion 114 connected to the needle portion 112, and a sheet-like sheet portion 116 connected to the frustum portion 114. The tapered-shaped needle portion 112 and the frustum portion 114 configure the needle-like protruding portion 110. The term "sheet-like" means a shape in which principal surfaces having a large area have a small thickness and are flat as a whole, and the principal surface is not necessarily flat completely.

A plurality of frustum portions 114 is formed on the surface of the sheet portion 116 (only one frustum portion 114 is shown in FIG. 1). The frustum portion 114 has two bottom surfaces and has a stereoscopic structure surrounded by a pyramidal surface. Out of the two bottom surfaces of the frustum portion 114, a bottom surface (lower base) having a larger area is connected to the sheet portion 116. Out of the two bottom surfaces of the frustum portion 114, a bottom surface (upper base) having a smaller area is connected to the needle portion 112. That is, out of the two bottom surfaces of the frustum portion 114, a bottom surface in a direction in which the bottom surface is separated from the sheet portion 116 has a smaller area.

The needle portion 112 has a gradually tapered shape and the needle portion 112 has a shape having a large area at a bottom surface and having the smallest area at a tip end separated from the bottom surface. Since the bottom surface of the needle portion 112 having a large area is connected to the bottom surface of the frustum portion 114 having a small area, the needle portion 112 has a gradually tapered shape in a direction in which the needle portion is separated from the frustum portion 114. Accordingly, the needle portion 112 has a shape in which the needle-like protruding portion 110 formed of the needle portion and the frustum portion 114 is tapered from the sheet portion 116 to the tip end as a whole. 4 to 2,500 of a plurality of needle-like protruding portions 110 are provided on the sheet portion 116. However, the number of needle-like protruding portions is not limited to the above number.

In FIG. 1, the frustum portion 114 has a truncated cone shape, and the needle portion 112 has a cone shape. The shape of a tip end of the needle portion 112 can be appropriately changed to a curved surface having a radius of curvature of 0.01 μm or more and 50 μm or less, a flat surface, or the like in accordance with the degree of insertion of the needle portion 112 into the skin.

FIG. 2 shows a needle-like protruding portion 110 having another shape. In FIG. 2, the frustum portion 114 has a truncated square pyramid shape and the needle portion 112 has a quadrangular pyramid shape.

Figure 3A:
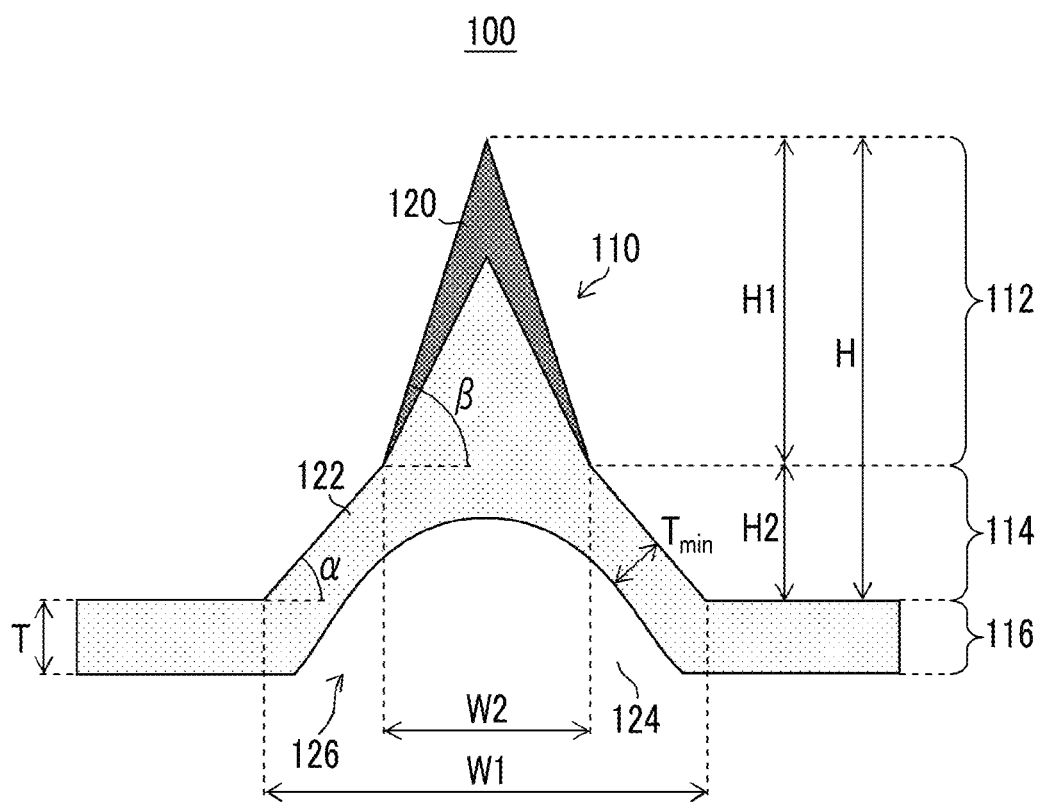
FIG. 3A is a cross-sectional view showing the needle-like protruding portions of the transdermal absorption sheets shown in FIGS. 1 and 2.
Figure 3B:
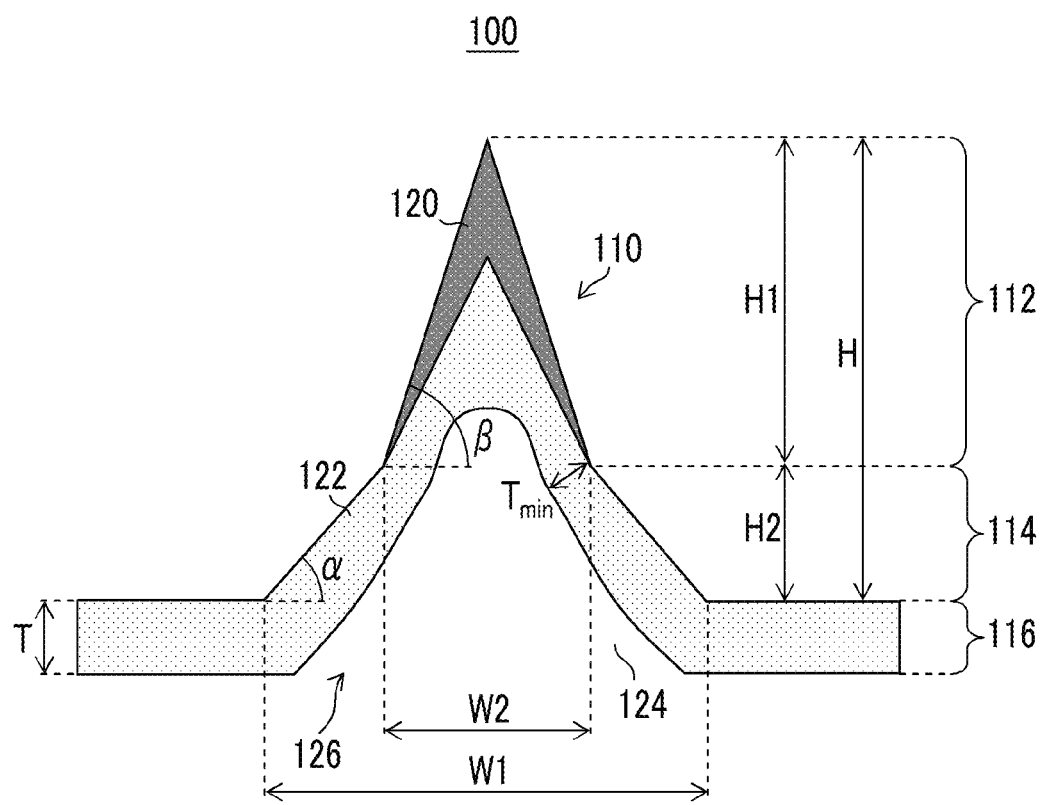
FIG. 3B is a cross-sectional view showing the needle-like protruding portions of the transdermal absorption sheets shown in FIGS. 1 and 2.

FIGS. 3A and 3B are cross-sectional views showing the transdermal absorption sheets 100 shown in FIGS. 1 and 2, respectively. As shown in FIGS. 3A and 3B, the transdermal absorption sheet 100 is formed of a first layer 120 containing a drug and a second layer 122 not containing a drug.

Here, the expression "containing a drug" means that the transdermal absorption sheet contains a drug in an amount such that the effect of the drug is exhibited in the case in which the transdermal absorption sheet 100 punctures the body surface. In addition, the expression "not containing a drug" means that the transdermal absorption sheet does not contain a drug in an amount such that the effect of the drug is exhibited, and the range of the amount of drug includes a range from 0, at which the transdermal absorption sheet does not contain a drug at all, to the amount of the drug in which the effect of the drug is exhibited. The first layer 120 containing a drug is formed at the tip end of the needle-like protruding portion 110 (the tip end of the needle portion 112). The drug can be effectively delivered into the skin by forming the first layer 120 at the tip end of the needle-like protruding portion 110. Hereinafter, the expression "containing a predetermined amount of drug" is referred to as "containing a drug" and the expression "not containing a predetermined amount of drug" is referred to as "not containing a drug" in some cases.

In the part of the needle portion 112 other than the first layer 120, the second layer 122 not containing a drug is formed. The frustum portion 114 is formed of the second layer 122. The sheet portion 116 is formed of the second layer 122. The distribution of the first layer 120 and the second layer 122 forming the needle portion 112, the frustum portion 114, and the sheet portion 116 can be appropriately set.

The thickness T of the sheet portion 116 is preferably in a range of 10 μm to 2,000 μm and more preferably in a range of 10 μm to 1,000 μm. A width W1 of the bottom surface (lower base) in which the frustum portion 114 and the sheet portion 116 are in contact with each other is preferably in a range of 100 μm to 1,500 μm and more preferably in a range of 100 μm to 1,000 μm. A width W2 of the bottom surface (upper base) in which the frustum portion 114 and the needle portion 112 are in contact with each other is preferably in a range of 100 μm to 1,500 μm and more preferably in a range of 100 μm to 1,000 μm. It is preferable that the width W1 and the width W2 satisfy the relationship of W1>W2 in the above numerical value range. The height H of the needle-like protruding portion 110 is preferably in a range of 100 μm to 2,000 μm and more preferably in a range of 200 μm to 1,500 μm. In addition, H1/H2 that is a ratio between a height H1 of the needle portion 112 and a height H2 of the frustum portion 114 is preferably in a range of 1 to 10 and more preferably in a range of 1.5 to 8. In addition, the height H2 of the frustum portion 114 is preferably in a range of 10 μm to 1,000 μm.

An angle α formed between the side surface of the frustum portion 114 and a surface parallel with the surface of the sheet portion 116 is preferably in a range of 10° to 60° and more preferably in a range of 20° to 50°. In addition, an angle β formed between the side surface of the needle portion 112 and a surface parallel to the upper base of the frustum portion 114 is preferably in a range of 45° to 85° and more preferably in a range of 60° to 80°.

The angle β may be equal to the angle α but the angle β is preferably equal to or greater than the angle α. This is because the needle-like protruding portion 110 easily punctures the skin.

In a first embodiment, as shown in FIG. 3A, at least one of the needle-like protruding portions 110 has a cavity portion 124 extending from the sheet portion 116 to the frustum portion 114. In addition, as shown in FIG. 3B, at least one of the needle-like protruding portions 110 has a cavity portion 124 extending from the sheet portion 116 to the needle portion 112 through the frustum portion 114.

The cavity portion 124 has an opening 126 on the sheet portion 116 side and means a space in the needle-like protruding portion 110, that is, a space in the frustum portion 114, or a space in the needle portion 112 through the frustum portion 114. The cavity portion 124 is a space that is not completely embedded in the needle-like protruding portion 110 and does not pass through the needle-like protruding portion 110.

The cavity portion 124 is not particularly limited in shape as long as the cavity portion extends to at least the frustum portion 114. However, regarding the shape of the cavity portion 124, it is preferable that the cavity portion 124 is entirely formed in a dome shape as shown in FIG. 3A, or the cavity portion 124 is partially formed in a dome shape as shown in FIG. 3B.

The term "dome shape" refers to a shape having a curved surface having a certain radius of curvature and a hemispherical shape can be exemplified. However, the shape thereof is not limited to the hemispherical shape and it is not necessary that the radius of curvature is uniform on the entire curved surface.

The expression "the cavity portion 124 is entirely formed in a dome shape" means a case in which as shown in FIG. 3A, the cavity portion 124 is formed by a curved surface.

The expression "the cavity portion 124 is partially formed in a dome shape" means a case in which as shown in FIG. 3B, a part of the tip end portion of the cavity portion 124 included in the needle portion 112 is formed by a curved surface. The dome shape of the tip end portion may not be present in the needle portion 112 and may be present in the frustum portion 114.

By forming the cavity portion 124 in a dome shape, the structure of the needle-like protruding portion 110 can be maintained against an impact or pressure at the time of puncture.

In the case in which the cavity portion 124 is formed in a dome shape, the radius of curvature for defining the curved surface is preferably 10 µm or more. That is, the cavity portion is preferably has a structure not having an angle of a radius of curvature of less than 10 µm. By setting the radius of curvature to 10 µm or more, stress can be prevented from being concentrated on the needle-like protruding portion 110 and thus the needle-like protruding portion 110 is prevented from collapsing. The radius of curvature is preferably 200 µm or less in a case of considering the size of the needle-like protruding portion 110.

The size of the cavity portion 124 is not particularly limited. However, the size of the cavity portion 124 is preferably set such that the thickness T n of the thinnest part of the needle-like protruding portion 110 having the cavity portion 124 is equal to or smaller than the thickness T of the sheet portion 116. The thickness T of the sheet portion 116 means the average thickness of the sheet portion 116. The thickness $T_{min}$ is preferably in a range of 10 µm to 500 µm and more preferably in a range of 10 µm to 100 µm. The thickness $T_{min}$ of the thinnest part is the thickness of the thinnest thickness part of the needle-like protruding portion 110 when viewed from the cavity portion 124.

The ratio of the cavity portion 124 occupying the needle-like protruding portion 110 is preferably 10% to 80% and more preferably 20% to 60%. Within this range, the strength of the needle-like protruding portion 110 can be maintained.

Figure 4A:
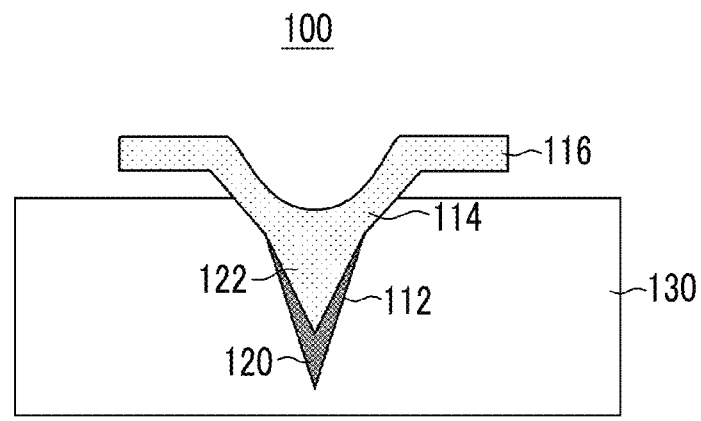
FIG. 4A is an illustration showing a state in which a drug in the transdermal absorption sheet is delivered into a skin.
Figure 4B:
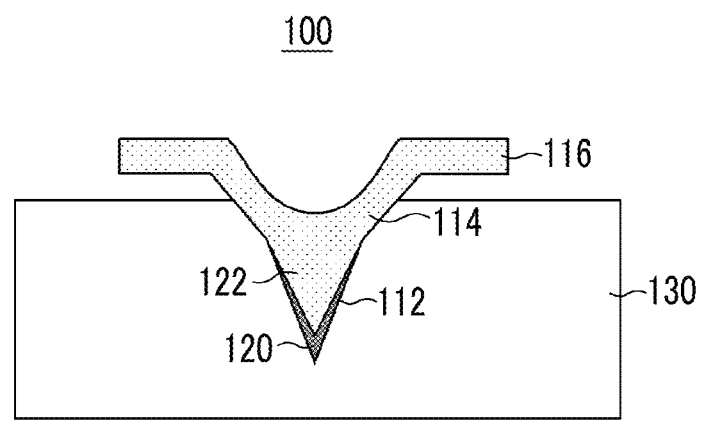
FIG. 4B is an illustration showing a state in which a drug in the transdermal absorption sheet is delivered into a skin.
Figure 4C:
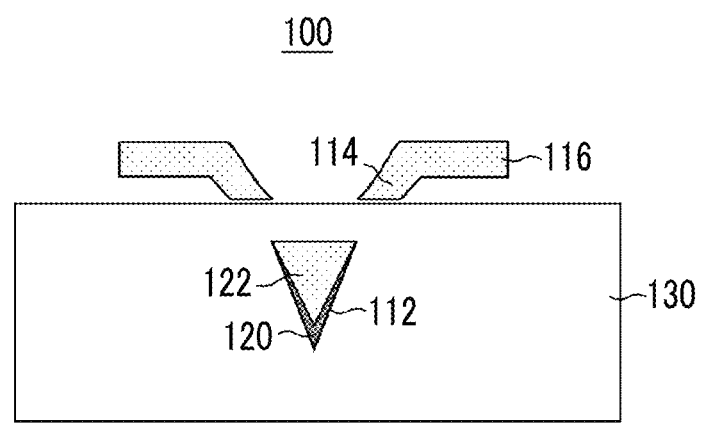
FIG. 4C is an illustration showing a state in which a drug in the transdermal absorption sheet is delivered into a skin.

FIGS. 4A to 4C are illustrations showing a state in which the drug in the transdermal absorption sheet is delivered into the skin. FIG. 4A shows a state immediately after the needle-like protruding portion 110 of the transdermal absorption sheet 100 is stuck into a skin 130. The needle portion 112 is located in the skin 130 and the first layer 120 containing a drug is arranged in the skin 130. The cavity portion 124 extends from the sheet portion 116 to a part of the frustum portion 114.

FIG. 4B shows a state in which several minutes have passed after the needle-like protruding portion 110 of the transdermal absorption sheet 100 is stuck into the skin 130. The first layer 120 forming the needle portion 112 is dissolved and the drug in the first layer 120 is delivered into the skin 130. Since the first layer 120 is dissolved, the size of the first layer 120 is reduced compared to the state immediately after the needle-like protruding portion of the transdermal absorption sheet is stuck into the skin 130. The second layer 122 in the skin 130 is dissolved and the size of the second layer 122 is reduced in the same manner.

FIG. 4C shows a state in which several minutes has passed from the state in FIG. 4B. The first layer 120 and the second layer 122 forming the needle portion 112 are further dissolved. In the case in which the second layer 122 is dissolved before reaching the cavity portion 124, the needle-like protruding portion 110 including the first layer 120 and the second layer 122 is separated from the sheet portion 116 and thus the needle-like protruding portion 110 can remain in the skin 130.

The entire periphery of the needle-like protruding portion 110 is brought into contact with the skin 130, the body fluid, and the needle solution. Since the contact area of the needle-like protruding portion 110, the skin 130, the body fluid, and the needle solution is large, the dissolution rate of the second layer 122 is accelerated and the entire periphery of the first layer 120 is brought into contact with the skin 130, the body fluid, and the needle solution. As a result, the contact area of the first layer 120, the skin 130, the body fluid, and the needle solution is large, the dissolution rate of the first layer 120 can be accelerated.

The cavity portion 124 may be formed so as to extend from the sheet portion 116 to at least the frustum portion 114 in the needle-like protruding portion 110, that is, as shown in FIG. 3A, the cavity portion 124 may be formed in a part of the frustum portion 114. Further, the cavity portion 124 is preferably formed so as to extend from the sheet portion 116 to the needle portion 112 in the needle-like protruding portion 110 as shown in FIG. 3B, that is, in the needle portion 112. By arranging the cavity portion 124 in the needle portion 112, the first layer 120 and the second layer 122 can be separated in the early stage.

In addition, the thickness $T_{min}$ of the thinnest part of the needle-like protruding portion 110 having the cavity portion 124 is preferably set to be equal to or smaller than the thickness T of the sheet portion 116. By setting the thickness $T_{min}$ to be in the above range, the shape of the sheet portion can be maintained at the time of puncture and the puncture pressure can be uniformly maintained.

In the case in which the thickness T of the sheet portion 116 is smaller than the thickness $T_{min}$, in the case in which the sheet portion 116 and the skin are brought into contact with each other at the time of puncture, there is a possibility that the sheet portion 116 may be dissolved faster than the needle-like protruding portion 110. In the case in which the shape of the sheet portion 116 is not maintained at the time of puncture, there is a case in which the puncture pressure is hardly uniformly maintained.

At least one needle-like protruding portion 110 of the plurality of needle-like protruding portions 110 to be formed in one transdermal absorption sheet 100 may have the cavity portion 124 extending from the sheet portion 116 to the frustum portion 114. In the case in which the needle-like protruding portion 110 including the cavity portion 124 extending to the frustum portion 114 and the needle-like protruding portion 110 not including the cavity portion 124 are present in a mixed manner in one transdermal absorption sheet 100, the dissolution rate of the drug of one transdermal absorption sheet 100 can be controlled. The needle-like protruding portion 110 including the cavity portion 124 may be arranged at a specific position of one transdermal absorption sheet 100 or may be arranged at a random position of one transdermal absorption sheet 100.

The number of needle-like protruding portions 110 having the cavity portion 124 is preferably in a range of 20% to 100% with respect to the total number of needle-like protruding portions 110. Within this range, control of the dissolution rate is easy.

Figure 5:
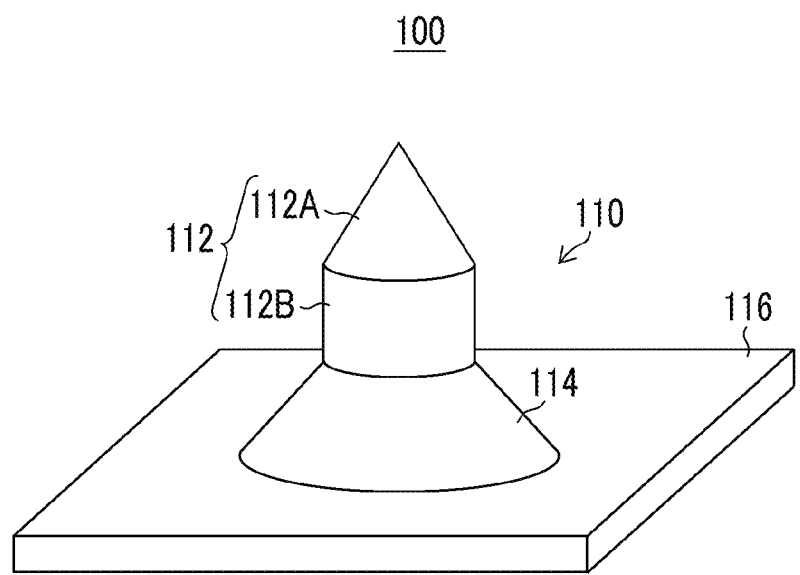
FIG. 5 is a perspective view showing a transdermal absorption sheet having a needle-like protruding portion of another shape.
Figure 6:
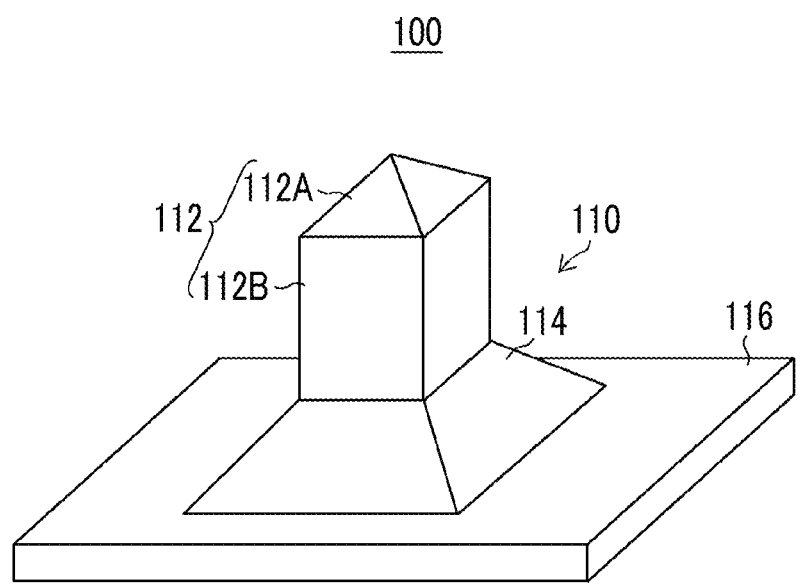
FIG. 6 is a perspective view showing a transdermal absorption sheet having a needle-like protruding portion of another shape.

FIGS. 5 and 6 show needle-like protruding portions 110 having other shapes. The transdermal absorption sheets 100 shown in FIGS. 1 and 5 and the transdermal absorption sheets 100 shown in FIGS. 2 and 6 are the same in shape of the frustum portion 114 but are different in shape of the needle portion 112, respectively. Each needle portion 112 shown in FIGS. 5 and 6 has a tapered needle-like portion (tapered tip end portion, tapered tip part) 112A and a cylindrical body portion 112B. The tapered needle-like portion 112A has a shape in which the bottom surface has a wide area and the tip end apart from the bottom surface has the smallest area. The cylindrical body portion 112B has two facing bottom surfaces and the two facing bottom surfaces have almost the same area. The bottom surface of the needle-like portion 112A having a wide area is connected to one bottom surface of the body portion 112B. In addition, the other bottom surface of the body portion 112B is connected to the bottom surface of the frustum portion 114 having a narrow area.

The needle-like portion 112A shown in FIG. 5 has a conical shape and the body portion 112B has a columnar shape. The needle-like portion 112A shown in FIG. 6 has a quadrangular pyramid shape and the body portion 112B has a quadrangular shape.

Since the needle portion 112 has the body portion 112B, the needle portion 112 is formed to have a shape having a fixed cross-sectional area in a direction apart from the frustum portion 114. The tapered needle-like portion 112A of the needle portion 112 has a shape tapered in a direction apart from the body portion 112B. The needle portion 112 has a tapered shape as a whole. According to a degree of insertion of the needle portion 112 into the skin, the shape of the tip end of the needle portion 112 can be appropriately changed to have a curved surface of a radius of curvature of 0.01 µm or more and 50 µm or less, a flat surface, or the like.

Figure 7A:
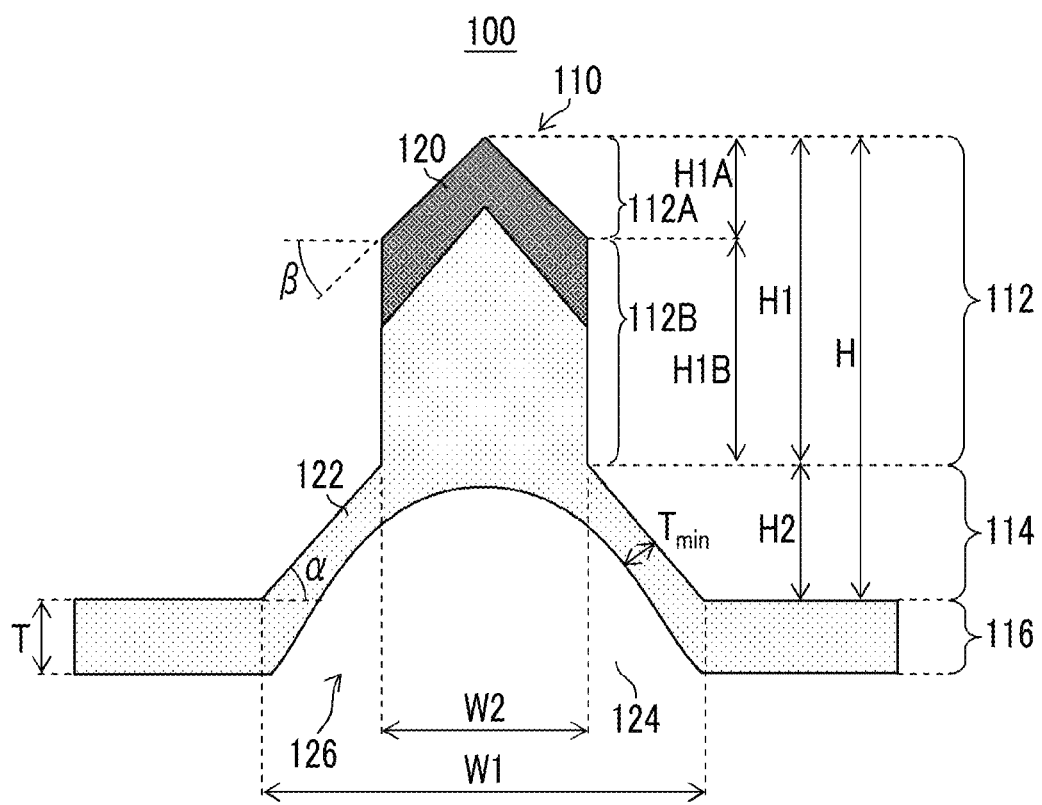
FIG. 7A is a cross-sectional view showing the needle-like protruding portions of the transdermal absorption sheets shown in FIGS. 5 and 6.
Figure 7B:
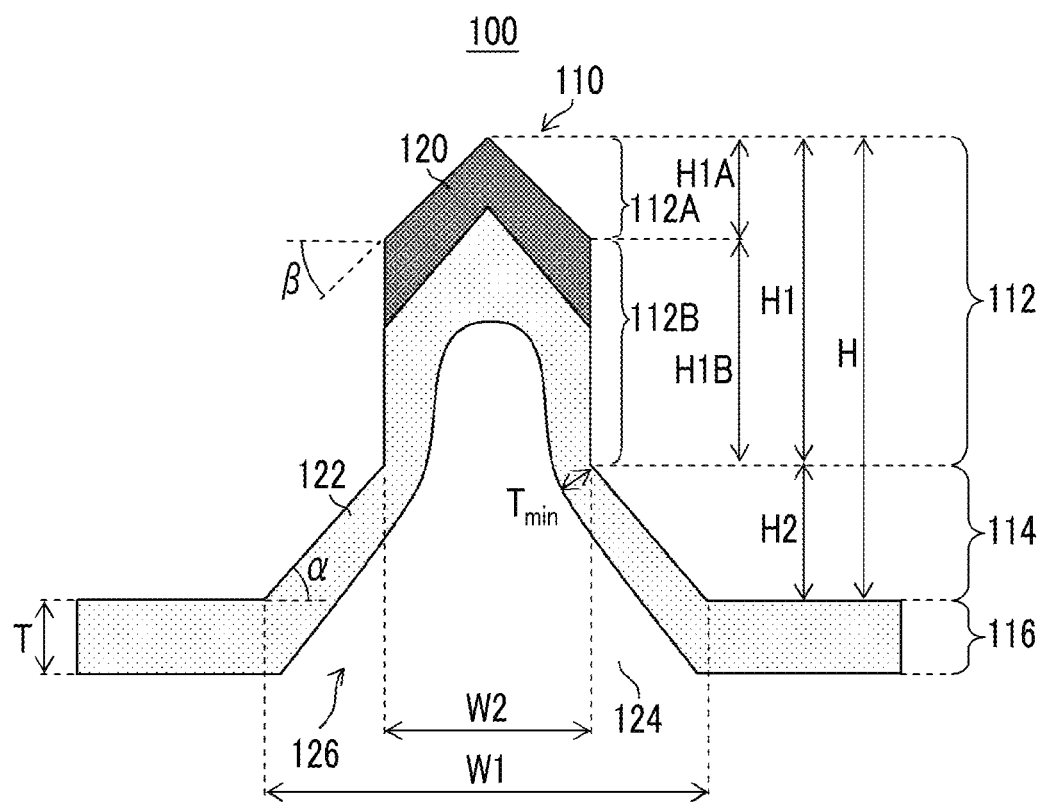
FIG. 7B is a cross-sectional view showing the needle-like protruding portions of the transdermal absorption sheets shown in FIGS. 5 and 6.

FIGS. 7A and 7B are cross-sectional views showing the transdermal absorption sheets 100 shown in FIGS. 5 and 6. As shown in FIGS. 7A and 7B, the transdermal absorption sheet 100 is formed of the first layer 120 containing a drug and the second layer 122 not containing a drug. The first layer 120 containing a drug is formed at the tip end of the needle-like protruding portion 110 (the tip end of the needle portion 112). By forming the first layer 120 at the tip end of the needle-like protruding portion 110, the drug can be effectively delivered into the skin.

In the part of the needle portion 112 other than the first layer 120, the second layer 122 not containing a drug is formed. The frustum portion 114 is formed of the second layer 122. The sheet portion 116 is formed of the second layer 122. The distribution of the first layer 120 and the second layer 122 forming the needle portion 112, the frustum portion 114, and the sheet portion 116 can be appropriately set.

The thickness T of the sheet portion 116, the width W1 of the lower base of the frustum portion 114, the width W2 of the upper base of the frustum portion 114, the height H of the needle-like protruding portion 110, and the height H2 of the frustum portion 114 can be set to be the same as the lengths in the transdermal absorption sheet 100 shown in FIGS. 3A and 3B. H1/H2 that is a ratio between the height H1 of the needle portion 112 and the height H2 of the frustum portion 114 can be set to be the same as the ratio in the transdermal absorption sheet 100 shown in FIGS. 3A and 3B.

H1B/H1A that is a ratio between a height H1A of the needle-like portion 112A and a height H1B of the body portion 112B is in a range of 0.1 to 4 and preferably in a range of 0.3 to 2.

The angle α, formed between the side surface of the frustum portion 114 and a surface parallel to the surface of the sheet portion 116 is in a range of 10° to 60° and preferably in a range of 20° to 50°. In addition, the angle β formed between the side surface of the needle-like portion 112A and a surface parallel to the bottom surface of the body portion 112B is in a range of 45° to 85° and preferably in a range of 60° to 80°.

The angle β is preferably equal to or greater than the angle α. This is because the needle-like protruding portion 110 is easily inserted into the skin.

In a second embodiment, as shown in FIG. 7A, at least one needle-like protruding portion 110 has a cavity portion 124 extending from the sheet portion 116 to the frustum portion 114. In addition, as shown in FIG. 7B, at least one needle-like protruding portion 110 has a cavity portion 124 extending from the sheet portion 116 to the needle portion 112 through the frustum portion 114.

The cavity portion 124 has the same shape as in the description of FIGS. 3A and 3B. In addition, the description of the shape and size of the cavity portion 124 are the same as in the description of FIGS. 3A and 3B. The description of entirely forming the cavity portion 124 in a dome shape and partially forming the cavity portion 124 in a dome shape is the same as in the description of FIGS. 3A and 3B. The description of the thickness $T_{min}$ of the thinnest part of the needle-like protruding portion 110 having the cavity portion 124 is the same as in the description of FIGS. 3A and 3B.

In the embodiment, the transdermal absorption sheets 100 having the needle-like protruding portions 110 shown in FIGS. 1, 2, 5, and 6 are described but the shape of the transdermal absorption sheet 100 is not limited to these shapes.

(Mold)

Figure 8A:
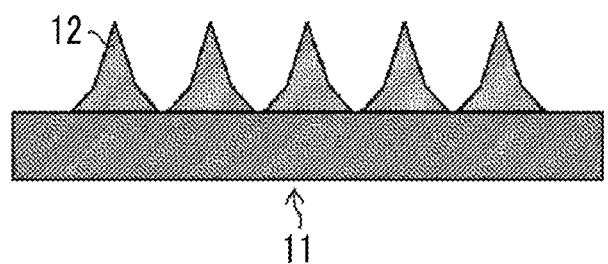
FIG. 8A is a step view of a method of producing a mold.
Figure 8B:
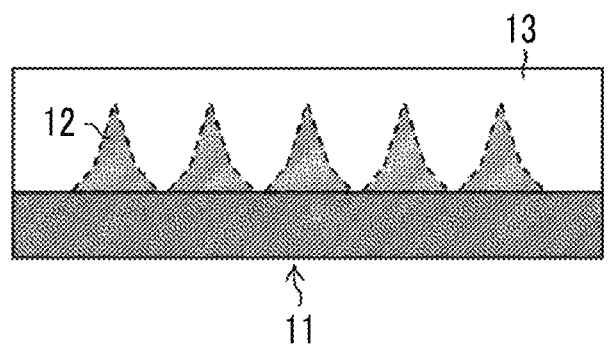
FIG. 8B is a step view of the method of producing a mold.
Figure 8C:
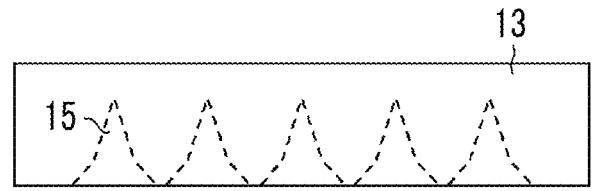
FIG. 8C is a step view of the method of producing a mold.

FIGS. 8A to 8C are step views showing a step of producing a mold (form).

As shown in FIG. 8A, first, an original plate for producing a mold for producing a transdermal absorption sheet is produced.

There are two kinds of methods of producing the original plate 11. The first method includes applying a photo resist to a Si substrate, and exposing and developing the photo resist. Then, etching by reactive ion etching, (RIE) or the like is performed to produce a plurality of protruding portions 12, each having the same shape as the needle-like protruding portion of the transdermal absorption sheet, in arrays on the surface of the original plate 11. In addition, in the case of performing etching such as RIE to form the protruding portion 12 on the surface of the original plate 11, the protruding portion 12 can be formed by performing etching from an oblique direction while rotating the Si substrate.

As the second method, there is a method including processing a metal substrate of stainless steel, an aluminum alloy, Ni, or the like using a cutting tool such as a diamond bite to produce a plurality of protruding portions 12 in arrays on the surface of the original plate 11.

Next, as shown in FIG. 8B, a mold 13 is produced using the original plate 11. In order to produce a normal mold 13, a method using Ni electroforming or the like is generally used. Since the original plate 11 has the protruding portions 12 having a conical shape with a sharp tip end or a pyramid shape (for example, a quadrangular pyramid shape), the shape of the original plate 11 is accurately transferred to the mold 13, and the mold 13 can be peeled off from the original plate 11. Four methods that make possible to produce the mold 13 at a low cost are considered.

The first method is a method in which a silicone resin obtained by adding a curing agent to polydimethylsiloxane (PDMS, for example, SYLGARD (registered trademark) 184, manufactured by Dow Corning Corporation) is poured into the original plate 11 and cured by a heating treatment at 100° C., and then the mold 13 is peeled off from the original plate 11. The second method is a method in which an ultraviolet curable resin that is curable by ultraviolet irradiation is poured into the original plate 11 and irradiated with ultraviolet light in a nitrogen atmosphere, and then the mold 13 is peeled off from the original plate 11. The third method is a method in which a material obtained by dissolving a plastic resin such as polystyrene or polymethylmethacrylate (PMMA) in an organic solvent is poured into the original plate 11 which has been coated with a release agent, and is dried to volatilize the organic solvent for curing, and then the mold 13 is peeled off from the original plate 11. The fourth method is a method in which an inverted article is made by Ni electroforming.

In this manner, the mold 13 in which the needle-like recessed portions 15 having an inverted shape of the protruding portion 12 of the original plate 11 are arranged two-dimensionally is produced. The mold 13 produced in this manner is shown in FIG. 8C. Since the shape of the protruding portion 12 of the original plate 11 is the same as the shape of the needle-like protruding portion of the transdermal absorption sheet, as shown in FIG. 8C, the mold 13 having the plurality of needle-like recessed portions corresponding to the inverted shape of the needle-like protruding portion of the transdermal absorption sheet is produced. In addition, in any of the above three methods, the mold 13 can be easily produced any number of times.

Figure 9A:
FIG. 9A is a cross-sectional view showing a mold provided with a frame.
Figure 9B:
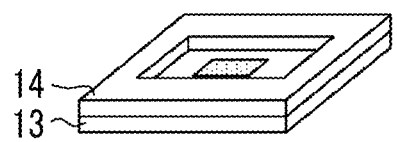
FIG. 9B is a perspective view showing the mold provided with the frame.
Figure 9C:
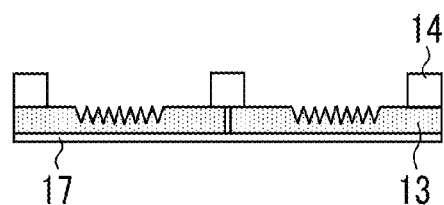
FIG. 9C is a cross-sectional view showing a mold provided with a frame.
Figure 9D:
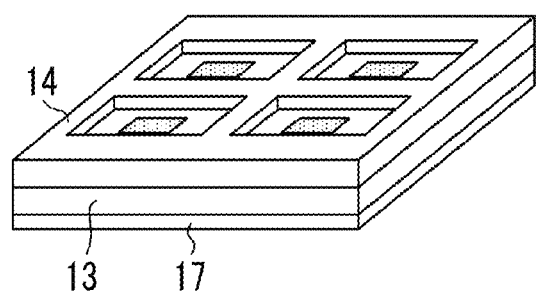
FIG. 9D is a perspective view showing the mold provided with the frame.

FIGS. 9A to 9D are views in which a frame 14 is installed on the mold 13 produced in FIG. 8C. FIGS. 9A and 9B are views in which the frame is provided at the periphery of the surface of the mold 13. FIGS. 9C and 9D are views in which the frame 14 is provided at the periphery of a plurality of molds 13 put together and on the inside of the mold. Provision of the frame 14 allows a solution of a polymer resin (hereinafter, also referred to as a "polymer solution") to be prevented from flowing to the outside of the mold 13 in the case of forming the functional film to have a desired film thickness.

At this time, the step between the mold 13 and the frame 14 is preferably 50 µm or more and 10 mm or less. In addition, the forms shown in FIGS. 9A to 9D are formed to enable the mold 13 and the frame 14 to be separated from each other, but the mold and the frame can be configured to be integrated together. In the case in which the mold and the frame can be separated from each other, the frame 14 can be removed in a drying step and a peeling-off step following the filling step.

As shown in FIGS. 9C and 9D, a plurality of molds 13 are joined onto a substrate 17 and the plurality of molds 13 are joined to one another, using an adhesive. Then, the frame 14 is installed at the periphery of the side surface of the mold 13 and on the inside of the mold 13.

Figure 10:
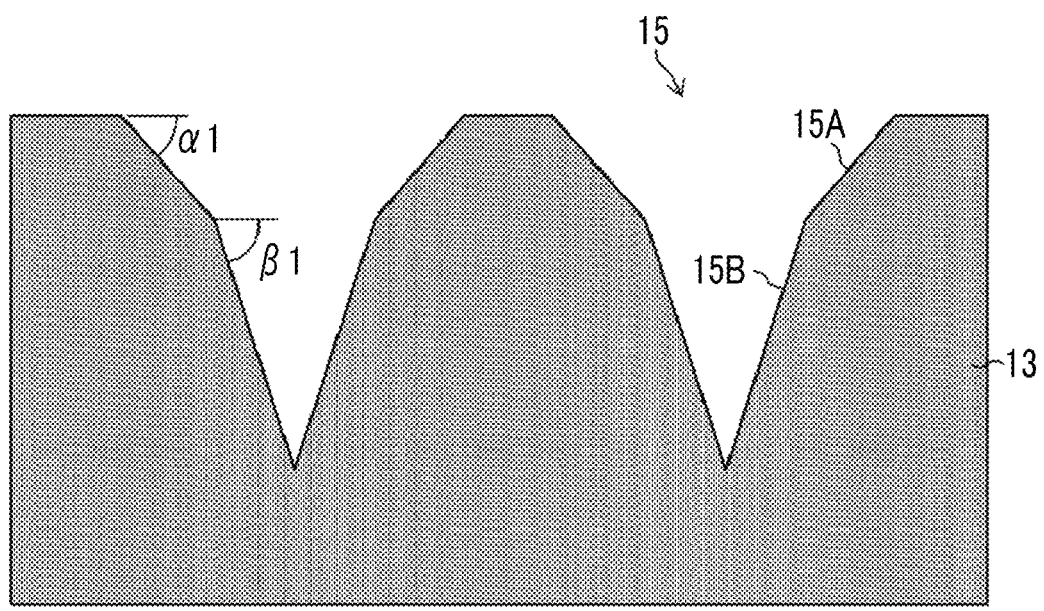
FIG. 10 is an enlarged view showing a part of the mold.

FIG. 10 is a partially enlarged view showing the mold 13. The needle-like recessed portion 15 is provided with a tapered inlet portion 15A that is narrower in a depth direction from the surface of the mold 13, and a tip end recessed portion 15B that is tapered in the depth direction. The angle α1 of the taper of the inlet portion 15A basically coincides the a formed between the side surface of the frustum portion of the transdermal absorption sheet and the sheet portion. In addition, the angle β1 of the taper of the tip end recessed portion 15B basically coincides the angle β formed between the side surface of the needle portion and the upper base of the frustum portion.

Figure 11:
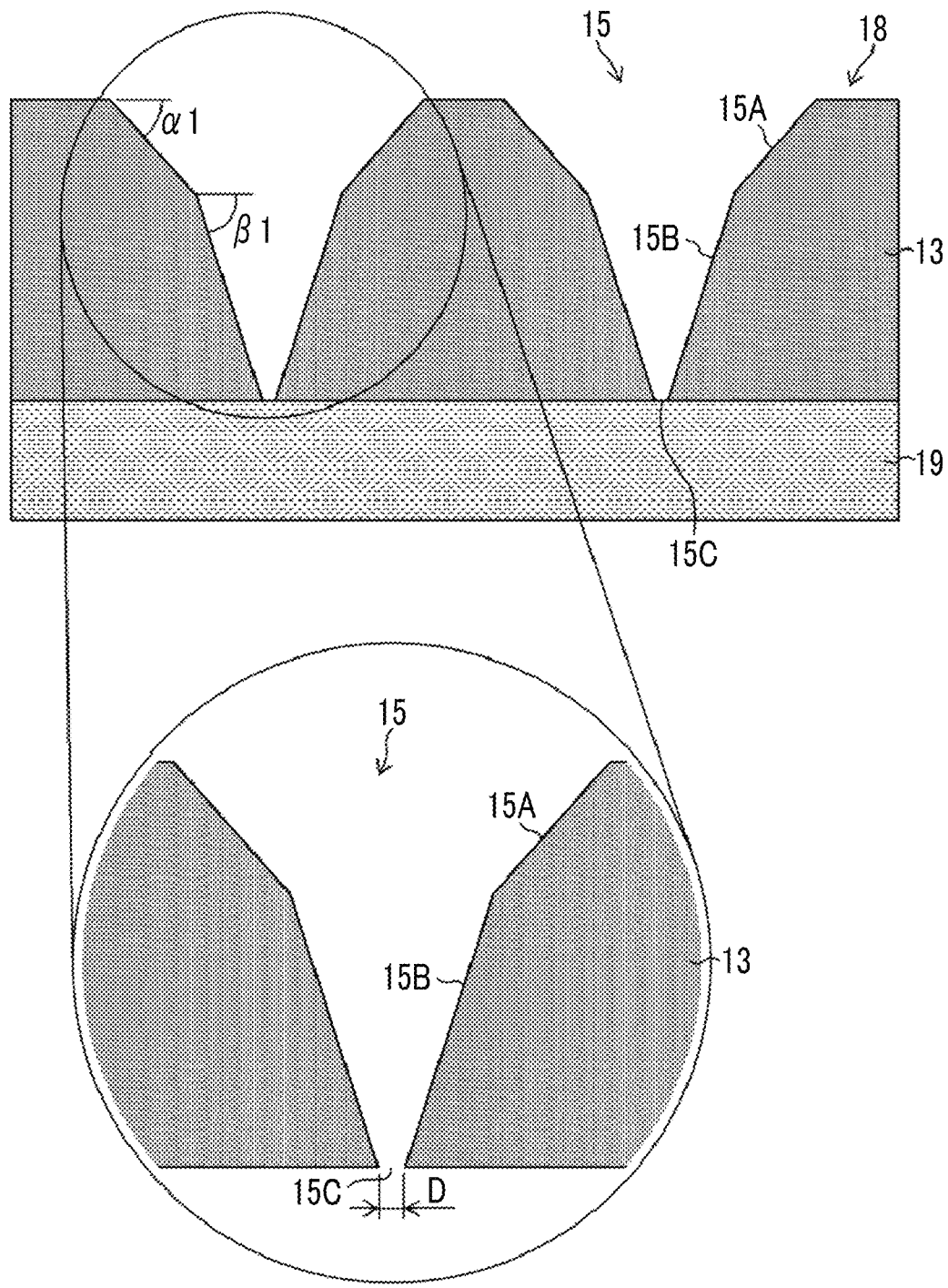
FIG. 11 is a partially enlarged view showing a mold complex.

FIG. 11 shows a more preferred embodiment of a mold complex 18 in performing a method of producing a transdermal absorption sheet. As shown in FIG. 11, the mold complex 18 includes a mold 13 in which a through-hole 15C is formed at the tip end of the needle-like recessed portion 15 and a gas permeable sheet 19 that is bonded to the through-hole 15C side of the mold 13 and is made of a material that is gas permeable, but is not liquid permeable. Through the through-hole 15C, the tip end of the needle-like recessed portion 15 communicates with the atmosphere through the gas permeable sheet 19. The expression "tip end of the needle-like recessed portion 15" means a side that is tapered in a depth direction of the mold 13 and is opposite to a side from which a drug solution that is a base solution is poured.

Using such a mold complex 18, only the air present in the needle-like recessed portion 15 can be removed from the needle-like recessed portion 15 via the through-hole 15C without permeation of the transdermal absorption material solution filling in the needle-like recessed portion 15. The transferability in the case in which the shape of the needle-like recessed portion 15 is transferred to the transdermal absorption material is improved, and thus it is possible to form a sharper needle-like protruding portion.

The diameter D of the through-hole 15C is preferably in a range of 1 to 50 µm. By adjusting the diameter within this range, air bleeding is easily performed, and the tip end portion of the needle-like protruding portion of the transdermal absorption sheet can be formed into a sharp shape. As the gas permeable sheet 19 made of a material that is gas permeable, but is not liquid permeable, for example, PORE-FLON (registered trademark, manufactured by Sumitomo Electric Industries, Ltd.) can be suitably used.

As the material used for the mold 13, an elastic raw material and a metallic raw material can be used. Of these, an elastic raw material is preferable and a raw material with high gas permeability is more preferable. The oxygen permeability, which is representative of the gas permeability, is preferably more than $1\times10^{-12}$ (mL/s·m·Pa) and more preferably more than $1\times10^{-10}$ (mL/s·m·Pa). By setting the gas permeability to be in the above range, the air present in the needle-like recessed portion 15 of the mold 13 can be removed from the mold 13. It is possible to produce a transdermal absorption sheet with few defects. Specific examples of such a material include materials obtained by melting general engineering a silicone resin (for example, SYLGARD 184 (registered trademark) or 1310ST), an ultraviolet curable resin, or a plastic resin (for example, polystyrene or polymethylmethacrylate (PMMA)) and materials obtained by dissolving any of the above resins in a solvent. Among these, a silicone rubber-based raw material can be suitably used because of the durability thereof to transfer by repeated pressurization and the good peelability thereof from the raw material. In addition, examples of the metallic raw material include Ni, Cu, Cr, Mo, W, Ir, Tr, Fe, Co, MgO, Ti, Zr, Hf, V, Nb, Ta, α-aluminum oxide, zirconium oxide, stainless steel (STAVAX (registered trademark) material, chrome alloy stainless tool steel), and alloys thereof. As the material for the frame 14, the same material as the material of the mold 13 can be used.

(Polymer Solution)

The polymer solution that is a solution of the polymer resin used in the embodiment is described.

In the embodiment, the expression "polymer solution containing the drug" or "drug-containing solution" means a polymer solution containing a predetermined amount of drug or a solution containing a predetermined amount of drug. In addition, the expression "polymer solution not containing the drug" or "non-drug-containing solution"

means a polymer solution not containing a predetermined amount of drug or a solution not containing a predetermined amount of drug.

Further, the polymer solution containing a drug is referred to as a drug solution and the polymer solution not containing a drug is referred to as a base solution in some cases.

Whether or not a predetermined amount of drug is contained in the solution can be determined based on whether or not the effect of the drug can be exhibited in the case in which the transdermal absorption sheet punctures the body surface. Accordingly, the expression "containing a predetermined amount of drug" means containing the drug in such an amount that the effect of the drug is exhibited in the case in which the transdermal absorption sheet punctures the body surface. The expression "not containing a predetermined amount of drug" means not containing the drug in such an amount that the effect of the drug is exhibited. The range of the amount of the drug includes a range from 0, at which the drug is not contained, to the amount of the drug at which the effect of the drug is exhibited.

As the raw material for the resin polymer used for the polymer solution, a biocompatible resin is preferably used. It is preferable to use, as such a resin, sugar such as glucose, maltose, pullulan, chondroitin sulfate, sodium hyaluronate, hydroxyethyl starch or hydroxypropyl cellulose, protein such as gelatin, or a biodegradable polymer such as polylactic acid and a lactic acid-glycolic acid copolymer. Among these, gelatin-based raw materials can be suitably used since the gelatin-based raw materials have adhesiveness with many base materials and have a high gel strength as materials to be gelated, and in the peeling-off step described later, the raw materials can be closely attached to the base material and a polymer sheet can be peeled off from the mold using the base material. The concentration of the resin is preferably such that 10% to 50% by mass of the resin polymer is contained in the polymer solution not containing a drug, while the concentration depends on the kind of the material. Additionally, a solvent used for dissolution may be other than hot water as long as the solvent has volatility, and methyl ethyl ketone, alcohol, or the like may be used. The drug to be supplied to the inside of the human body may concurrently be dissolved into the solution of the polymer resin in accordance with the application. The concentration of the polymer of the polymer solution containing a drug (the concentration of the polymer excluding the drug in the case in which the drug itself is a polymer) is preferably 0% to 40% by mass.

For a method for preparing the polymer solution, in the case in which a water-soluble polymer (gelatin or the like) is used, the solution may be prepared by dissolving water-soluble powder into water, and after the dissolution, adding a drug to the solution or putting and dissolving water-soluble polymer powder into a drug-containing solution dissolved therein. In the case in which the polymer resin is difficult to dissolve into water, the polymer resin may be dissolved on heating. The temperature can be appropriately selected as needed depending on the kind of the polymer material, but the material is preferably heated at about 60° C. or lower. Regarding the viscosity of the solution of the polymer resin, the viscosity of the drug-containing solution is preferably 100 Pa·s or less and more preferably 10 Pa·s or less. The viscosity of the non-drug-containing solution is preferably 2,000 Pa·s or less and more preferably 1,000 Pa·s or less. Appropriate adjustment of the viscosity of the solution of the polymer resin facilitates injection of the solution into the needle-like recessed portions of the mold. For example, the viscosity of the solution of the polymer resin can be measured with a capillary type viscometer, a falling ball type viscometer, a rotational type viscometer, or an oscillatory type viscometer.

(Drug)

The drug that the polymer solution contains is not particularly limited as long as the drug is a substance having bioactivity. The drug is preferably selected from peptide, protein, nucleic acid, polysaccharide, a vaccine, a medical compound, and a cosmetic component. In addition, it is preferable that the medical compound belongs to a water-soluble low-molecular-weight compound. Here, the low-molecular-weight compound refers to a compound in a range of a molecular weight of several hundreds to several thousands.

(Method of Producing Transdermal Absorption Sheet)

Figure 12:
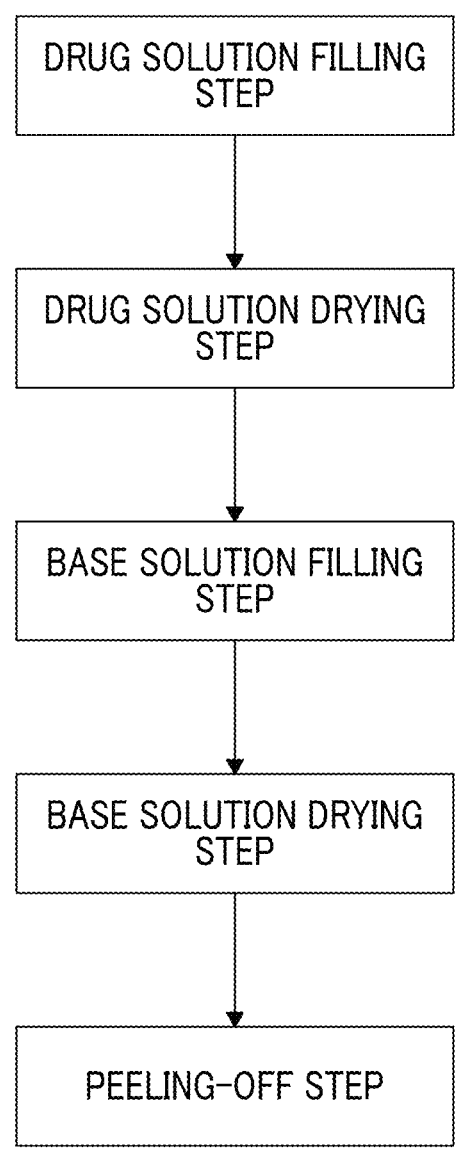
FIG. 12 is a flowchart of a method of producing a transdermal absorption sheet.

The method of producing the transdermal absorption sheet of the embodiment includes at least five steps of a drug solution filling step, a drug solution drying step, a base solution filling step, a base solution drying step, and a peeling-off step in this order as shown in FIG. 12.

(Drug Solution Filling Step)

Figure 13A:
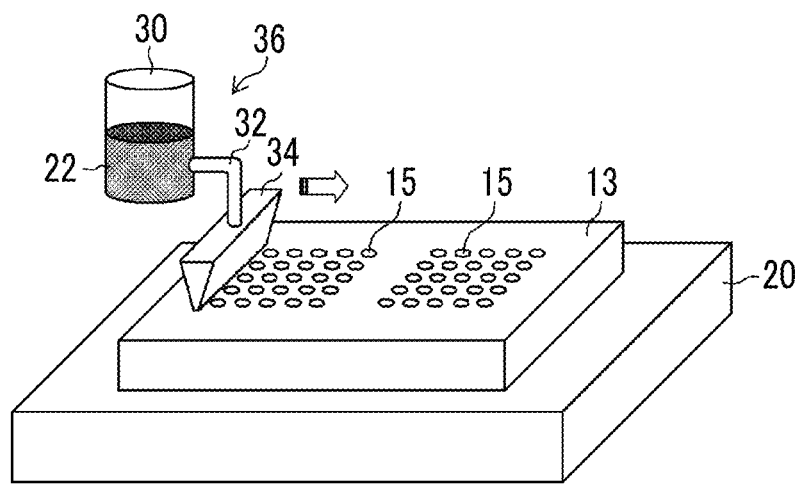
FIG. 13A is a schematic view showing a step of filling a needle-like recessed portion of a mold with a drug solution.

The method of producing the transdermal absorption sheet using the mold 13 will be described. As shown in FIG. 13A, the mold 13 with the two-dimensionally arranged needle-like recessed portions 15 is placed on a base 20. Two sets of a plurality of needle-like recessed portions 15, each set including 5×5 two-dimensionally arranged needle-like recessed portions 15, are formed in the mold 13. A liquid supply apparatus 36 which has a liquid feed tank 30 storing a drug solution 22 that is a polymer solution containing a drug, a pipe 32 connected to the liquid feed tank 30, and a nozzle 34 connected to a tip end of the pipe 32 is prepared. The drug solution 22 is discharged from the tip end of the nozzle 34.

Figure 14:
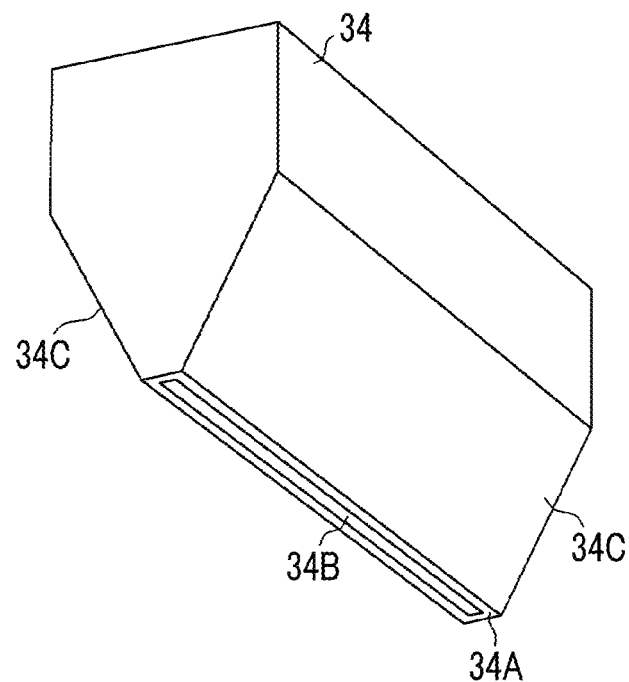
FIG. 14 is a perspective view showing a tip end of a nozzle.

FIG. 14 shows a schematic perspective view of the tip end portion of the nozzle. As shown in FIG. 14, the tip end of the nozzle 34 includes a lip portion 34A that has a flat surface on the tip end side, a slit-shaped opening portion 34B, and two inclined surfaces 34C that are widened along the lip portion 34A in a direction away from the opening portion 34B. The slit-shaped opening portion 34B, for example, allows a plurality of needle-like recessed portions 15 constituting one column to be simultaneously filled with the drug solution 22. The size (length and width) of the opening portion 34B is appropriately selected in accordance with the number of needle-like recessed portions 15 to be filled at a time.

An increased length of the opening portion 34B makes it possible to fill an increased number of needle-like recessed portions 15 with the drug solution 22 at a time. Thus, productivity can be improved.

Figure 15:
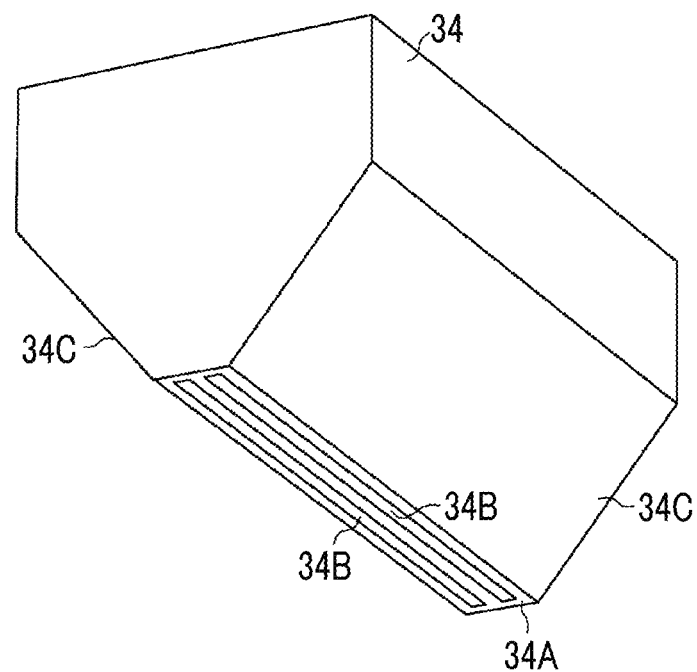
FIG. 15 is a perspective view showing a tip end of another nozzle.

FIG. 15 shows a schematic perspective view of a tip end portion of another nozzle. As shown in FIG. 15, the nozzle 34 has a lip portion 34A having a flat surface on the tip end side, two slit-shaped opening portions 34B, and two inclined surfaces 34C that are widened along the lip portion 34A in a direction away from the opening portion 34B. The two opening portions 34B, for example, allow a plurality of needle-like recessed portions 15 constituting two columns to be simultaneously filled with the drug solution 22 containing a drug.

As the material used for the nozzle 34, an elastic raw material and a metallic raw material may be used. For example, TEFLON (registered trademark), stainless steel, or titanium may be used.

Figure 13B:
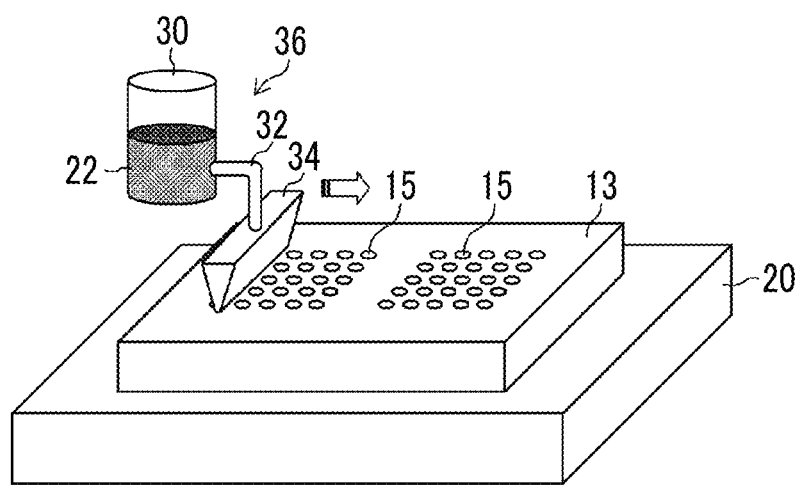
FIG. 13B is a schematic view showing the step of filling the needle-like recessed portion of the mold with the drug solution.

The filling step will be described with reference to FIG. 13B. As shown in FIG. 13B, the position of the opening portion 34B in the nozzle 34 is adjusted on the needle-like recessed portions 15. The lip portion 34A of the nozzle 34 is in contact with the surface of the mold 13 since the nozzle 34 that discharges the drug solution 22 is pressed against the mold 13. The drug solution 22 is supplied from the liquid supply apparatus 36 to the mold 13, and the needle-like recessed portions 15 are filled with the drug solution 22 through the opening portion 34B in the nozzle 34. In the embodiment, the plurality of needle-like recessed portions 15 constituting, one column are simultaneously filled with the drug solution 22. However, the present invention is not limited to this configuration. The needle-like recessed portions 15 may be filled with the drug, solution 22 one by one. In addition, by using the nozzle 34 shown in FIG. 15, the plurality of needle-like recessed portions 15 constituting the plurality of columns can be simultaneously filled with the drug solution 22 so that filling is performed on the plurality of columns at a time.

In the case in which the mold 13 is formed of a raw material having gas permeability, the drug solution 22 can be sucked by sucking from the back surface of the mold 13, thereby promoting filling of the inside of the needle-like recessed portions 15 with the drug solution 22.

Figure 13C:
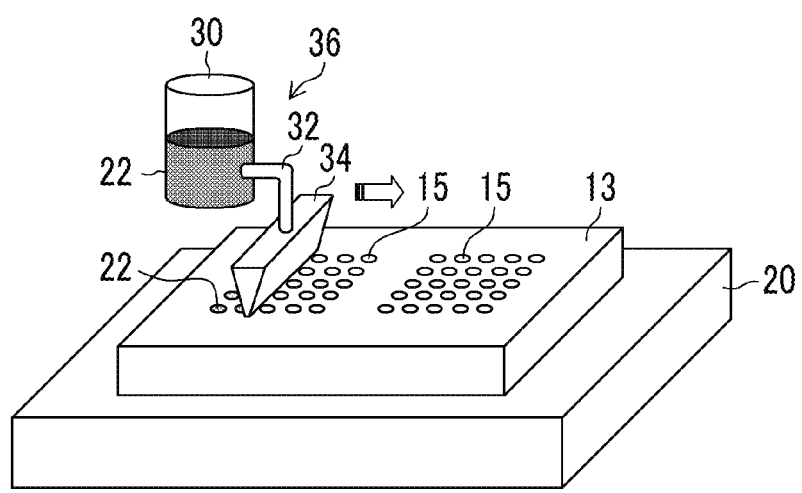
FIG. 13C is a schematic view showing the step of filling the needle-like recessed portion of the mold with the drug solution.

As shown in FIG. 13C, while bringing the lip portion 34A of the nozzle 34 into contact with the surface of the mold 13, the liquid supply apparatus 36 is relatively scanned in a direction perpendicular to a length direction of the opening portion 34B subsequent to the filling step in FIG. 13B. By scanning the surface of the mold 13 by the nozzle 34, the nozzle 34 is moved to the needle-like recessed portion 15 not filled with the drug solution 22. The position of the opening portion 34B of the nozzle 34 is adjusted on the needle-like recessed portions 15. The embodiment has been described with reference to the example in which the nozzle 34 is scanned. However, the mold 13 may be scanned.

Since the nozzle 34 is scanned on the surface of the mold 13 while the lip portion 34A of the nozzle 34 is brought into contact the surface of the mold 13, the nozzle 34 can scrape off the drug solution 22 remaining on the surface of the mold 13 excluding the needle-like recessed portions 15. This enables the drug solution 22 containing a drug to be prevented from remaining on the surface of the mold 13 excluding the needle-like recessed portions 15. In the embodiment, the inclined surfaces 34C of the nozzle 34 are arranged at a position perpendicular to the scanning direction indicated by the arrow. Accordingly, the nozzle 34 can be smoothly scanned on the surface of the mold 13.

In order to reduce damage to the mold 13 and to suppress deformation of the mold 13 due to compression as much as possible, the degree of pressurization of the nozzle 34 against the mold 13 in the case of scanning is preferably controlled. For example, the pressing force with which the nozzle 34 is pressed against the mold 13 or the pressing distance of the nozzle 34 against the mold 13 is preferably controlled. Furthermore, in order to prevent the drug solution 22 from remaining on the mold 13 excluding the needle-like recessed portions 15, at least one of the mold 13 or the nozzle 34 is desirably formed of a flexible, elastically deformable raw material.

The filling step shown in FIG. 13B and the moving step shown in FIG. 13C are repeated to fill a 5×5 two-dimensionally arranged needle-like recessed portions 15 with the drug solution 22. In the case in which the 5×5 two-dimensionally arranged needle-like recessed portions 15 are filled with the drug solution 22, the liquid supply apparatus 36 is moved to the adjacent 5×5 two-dimensionally arranged needle-like recessed portions 15, and the filling step in FIG. 13B and the moving step in FIG. 13C are repeated. The adjacent 5×5 two-dimensionally arranged needle-like recessed portions 15 are also filled with the drug solution 22.

The above filling step and scanning step may be in (1) a form in which the needle-like recessed portions 15 are filled with the drug solution 22 while the nozzle 34 is being scanned or (2) a form in which, while the nozzle 34 is in scanning, the nozzle 34 is temporarily stopped above the needle-like recessed portions 15 to fill the needle-like recessed portions 15 with the drug solution 22, and the nozzle 34 is scanned again after the filling. Between the filling step and the scanning step, the lip portion 34A of the nozzle 34 is pressed against the surface of the mold 13. The amount of the drug solution 22 discharged from the liquid supply apparatus 36 is preferably equal to the total volume of the plurality of needle-like recessed portions 15 of the mold 13 to be filled. The drug solution 22 is prevented from remaining on the surface of the mold 13 excluding the needle-like recessed portions 15 and thus wasting the drug can be reduced.

Figure 16:
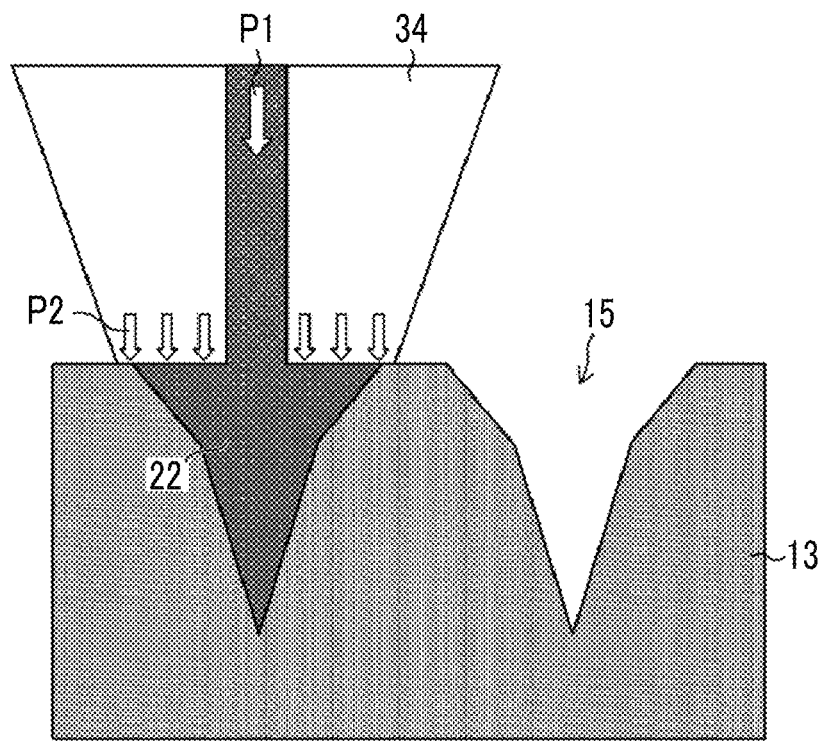
FIG. 16 is a partially enlarged view showing the tip end of the nozzle and the mold during filling.

FIG. 16 is a partially enlarged view of the tip end of the nozzle 34 and the mold 13 during filling of the needle-like recessed portions 15 with the drug solution 22. As shown in FIG. 16, filling of the inside of the needle-like recessed portions 15 with the drug solution 22 can be promoted by applying a pressuring force P1 into the nozzle 34. Moreover, in the case in which the needle-like recessed portions 15 is filled with the drug solution 22, a pressing force P2 with which the nozzle 34 is brought into contact with the surface of the mold 13 is preferably set to be equal to or greater than the pressuring force P1 in the nozzle 34. Setting the pressing force P2≥the pressuring force P1 enables the drug solution 22 to be restrained from leaking from the needle-like recessed portions 15 to the surface of the mold 13.

Figure 17:
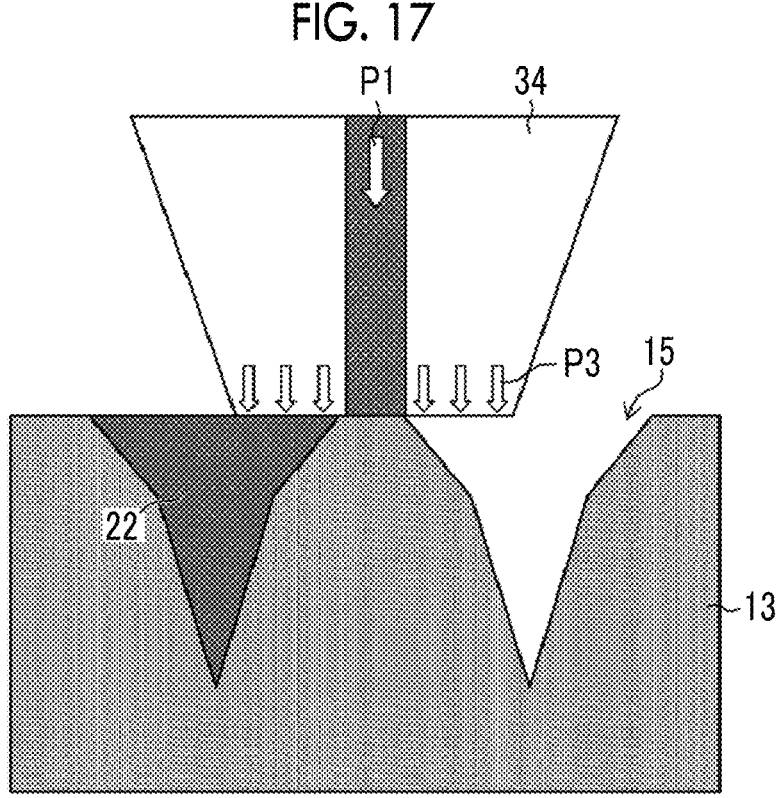
FIG. 17 is a partially enlarged view showing the tip end of the nozzle and the mold during scanning.

FIG. 17 is a partially enlarged view of the tip end of the nozzle 34 and the mold 13 during movement of the nozzle 34. In the case in which the nozzle 34 is scanned relative to the mold 13, a pressing force P3 with which the nozzle 34 is brought into contact with the surface of the mold 13 is preferably set to be smaller than the pressing force P2 with which the nozzle 34 is brought into contact with the surface of the mold 13 while filling is performed. This is intended to reduce damage to the mold 13 and to suppress deformation of the mold 13 associated with compression.

It is preferable that the lip portion 34A of the nozzle 34 is parallel to the surface of the mold 13. The posture of the nozzle 34 may be controlled by providing a joint driving mechanism at a mounting portion of the nozzle 34.

The pressing force and/or the pressing distance of the nozzle 34 to the mold 13 is/are preferably controlled by driving the nozzle 34 in a Z-axis direction in accordance with the surface shape of the mold 13. FIG. 18 is a schematic configuration diagram of a drug solution filling apparatus 48 capable of controlling the pressing force and/or the pressing distance. The drug solution filling apparatus 48 has a liquid supply apparatus 36 that has a liquid feed tank 30 storing a drug solution and a nozzle 34 mounted on the liquid feed tank 30, a Z-axis driving unit 50 that drives the liquid feed tank 30 and the nozzle 34 in the Z-axis direction, a suction base 52 for placing the mold 13 thereon, a X-axis driving unit 54 that drives the suction base 52 in a X-axis direction, a stand 56 that supports the apparatus, and a control system 58.

The case of controlling a pressing force to be constant will be described. The Z-axis driving unit 50 brings the nozzle 34 close to the mold 13 up to Z-coordinates in which a desired pressing force is obtained. While the nozzle 34 brought into contact with the mold 13 is scanned by the X-axis driving unit 54, the drug solution 22 is discharged while Z-axis coordinate control is performed such that the pressing force becomes constant. The contact pressure measuring method is not particularly limited, but for example, various load cells can be used, for example, under the suction base 52 or in place of the suction base 52. The load cell means a measuring instrument capable of measuring a force for compression in a thickness direction. The pressing force is an arbitrary pressure within a range of 1 to 1,000 kPa with respect to the mold 13, and is preferably controlled to be constant.

The case of controlling a pressing distance to be constant will be described. Before contact with the nozzle 34, the surface shape of the mold 13 is measured in advance. While the nozzle 34 brought into contact with the mold 13 is scanned by the X-axis driving unit 54, the value obtained by performing Z-axis coordinate offset such that a desired pressing distance is provided with respect to the surface shape of the mold 13 is supplied back to the Z-axis driving unit 50 by the control system 58.

The shape measuring method is not particularly limited. For example, an optical measuring instrument such as a non-contact-type laser displacement meter 60 or a contact-type probe-type step profiler can be used. Furthermore, the posture of the nozzle 34 in a slit direction may be controlled in accordance with the surface shape of the mold 13. The pressing distance is preferably controlled within a range of 1% to 15% with respect to the thickness of the mold 13. Through the operation with the control of the distance between the nozzle 34 and the mold 13 in the Z-axis direction by the Z-axis driving unit 50 in accordance with the shape of the mold 13, the compression deformation rate becomes uniform, and thus the accuracy of the filling amount can be improved.

Regarding the control of the pressing force and the pressing distance, the pressing force is preferably controlled in the case in which the pressing distance is small, and the pressing distance is preferably directly controlled in the case in which the pressing distance is large.

FIG. 19 is an illustration showing the relationship between the liquid pressure in the nozzle and the supply of the drug-containing solution. As illustrated in FIG. 19, the supply of the drug solution 22 is started before the nozzle 34 is positioned above the needle-like recessed portions 15. The reason for this is to securely fill the needle-like recessed portions 15 with the drug solution 22. Until the filling of the plurality of needle-like recessed portions 15 of 5×5 is completed, the drug solution 22 is continuously supplied to the mold 13. The supply of the drug solution 22 to the mold 13 is stopped before the nozzle 34 is positioned above needle-like recessed portions 15 in the fifth column. Therefore, it is possible to prevent the drug solution 22 from overflowing from the needle-like recessed portions 15. The liquid pressure in the nozzle 34 increases in a region where the nozzle 34 is not positioned above the needle-like recessed portions 15 in the case in which the supply of the drug solution 22 is started. Meanwhile, in the case in which the nozzle 34 is positioned above the needle-like recessed portions 15, the needle-like recessed portions 15 are filled with the drug solution 22, and the liquid pressure in the nozzle 34 decreases. That is, the liquid pressure repeatedly changes.

In the case in which the filling of the plurality of needle-like recessed portions 15 of 5×5 is completed, the nozzle 34 is moved to a plurality of adjacent needle-like recessed portions 15 of 5×5. Regarding the liquid supply, the supply of the drug solution 22 is preferably stopped in the case in which the nozzle is moved to the plurality of adjacent needle-like recessed portions 15 of 5×5. There is a distance between the needle-like recessed portions 15 in the fifth column and the needle-like recessed portions 15 in the next first column. In the case in which the drug solution 22 is continuously supplied therebetween during the scanning of the nozzle 34, the liquid pressure in the nozzle 34 may excessively increase. As a result, the drug solution 22 may flow to a region of the mold 13 excluding the needle-like recessed portions 15 from the nozzle 34. In order to suppress this problem, the supply of the drug solution 22 is preferably stopped.

The tip end of the nozzle 34 is preferably used after being cleaned in the case of performing the drug solution filling. This is because the accuracy of the filling amount of the drug solution 22 is reduced in a case in which a substance adheres to the surface of the lip portion 34A of the nozzle 34 before filling. In general, wiping using non-woven cloth is performed for cleaning. During wiping, the cleaning can be effectively performed in the case in which non-woven cloth is permeated with water, a solvent, or the like. After filling with the drug solution 22, there is a possibility that the drug solution may remain on the surface of the mold 13 in the case in which the nozzle 34 is separated from the mold 13. By performing suck back control for suction of the drug solution from the opening portion 34B of the nozzle 34 after completion of the filling of the needle-like recessed portions 15, an excessive amount of the drug solution 22 discharged can be sucked, and the liquid remaining on the surface of the mold 13 can thus be reduced.

In the drug solution filling step, the drug solution can be sucked from the through-hole 15C side using the mold complex 18 shown in FIG. 11 to fill the needle-like recessed portions 15 with the drug solution 22. This is because it is not particularly preferable that an air bubble is incorporated in the drug solution 22 since a variation occurs in the content of the drug.

In the case in which the filling of the needle-like recessed portions 15 with the drug solution 22 is completed, the process proceeds to the drug solution drying step, the base solution filling step, the base solution drying step, and the peeling-off step.

Figure 20A:
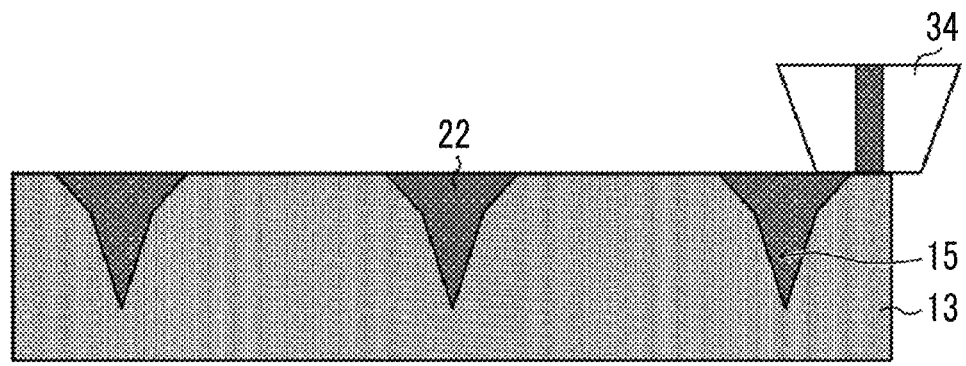
FIG. 20A is a schematic view showing a part of a step of producing a transdermal absorption sheet.

As shown in FIG. 20A, the needle-like recessed portions 15 of the mold 13 are filled with the drug solution 22 from the nozzle 34 in the drug solution filling step. The drug solution filling step is performed using the above-described method.

(Drug Solution Drying Step)

Figure 20B:
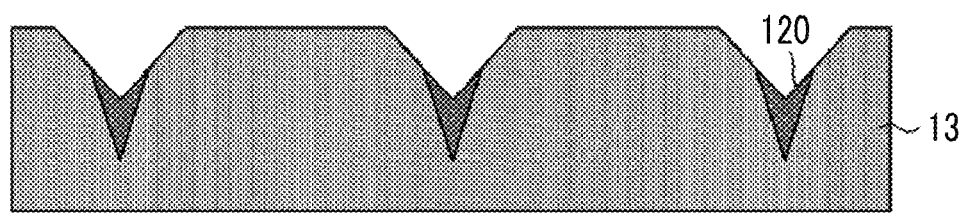
FIG. 20B is a schematic view showing a part of the step of producing a transdermal absorption sheet.

As illustrated in FIG. 20B, in the drug solution drying step, the drug solution 22 is dried and solidified, and thus first layers 120 containing a drug are formed in the needle-like recessed portions 15.

The drug solution drying step is a step of drying the drug solution 22 filled in the needle-like recessed portions 15 of the mold 13 and localizing the first layers 120 containing a drug at the tip ends of the needle-like recessed portions 15.

In addition, by optimizing the drying rate with the control of the temperature and humidity conditions of the drug solution drying step, it is possible to reduce fixing of the drug solution 22 to a wall surface of the mold 13 of the needle-like recessed portions 15, and the drying proceeds while the drug solution 22 is collected at the tip end of the needle-like recessed portion 15 by drying. For example, in an environment at a temperature of 23° C. and a relative humidity of 40% to 60% RH, the drying rate is high, and thus the drug solution 22 may be fixed to the wall surface of the mold 13 of the needle-like recessed portions 15 and it may be difficult to localize the drug solution 22 at the tip ends of the needle-like recessed portions 15 in some cases.

The drying rate of the drug solution 22 can be reduced by performing the drug solution drying step in an environment at a temperature of 1° C. to 10° C. Accordingly, the drug solution 22 can be localized at the tip ends of the needle-like recessed portions 15 without fixing the drug solution 22 to the wall surface of the mold 13. In the drug solution drying step in an environment at a temperature of 1° C. to 10° C., in the case in which the humidity is high, the drying rate of the drug solution 22 is reduced, and thus deterioration in productivity is caused. In the case in which the drug solution drying step is performed in an environment at a temperature of 1° C. to 10° C., an environment at a relative humidity of 1% to 59% is preferably provided, and an environment at a relative humidity of 21% to 39% is more preferably provided. In an environment in a temperature and humidity range of a temperature of 1° C. to 10° C. and a relative humidity range of 1% to 59%, it is possible to achieve high productivity and the localization of the drug solution 22 at the tip ends of the needle-like recessed portions 15 at the same time.

In order to provide an environment at a relative humidity of 1% to 59%, for example, the drug solution drying step is preferably performed in a constant-temperature chamber or a constant-temperature tank having a humidity adjustment function.

The drug solution 22 is preferably dried in a windless state in the drug solution drying step. Uneven drying occurs in the case in which the drug solution 22 is directly exposed to non-uniform wind. This is because, in a portion exposed to strong wind, the drying rate may be increased, the drug solution 22 may be fixed to the wall surface of the mold 13, and thus the localization of the drug solution 22 at the tip ends of the needle-like recessed portions 15 may be disturbed.

In order to realize the drying in a windless state, for example, a windshield is preferably installed. The windshield is installed so as not to directly expose the mold 13 to wind. As the windshield, a physical obstacle such as a lid, a hood, a screen, a fence, or the like is preferably installed since this is a simple method. In addition, in the case in which the windshield is installed, a vent hole or the like is preferably secured such that the installation space for the mold 13 is not in a sealed state. In the case in which the installation space is in a sealed state, water vapor in the sealed space may be saturated, and the drying of the drug solution 22 may not proceed. The vent hole is preferably formed such that the passage of vapor is possible, and is more preferably covered with a water vapor permeable film or the like to stabilize the air flow in the windshield. The drying time is appropriately adjusted in consideration of the shape of the needle-like recessed portion 15, the arrangement of the needle-like recessed portions 15, and the number of the needle-like recessed portions 15, the kind of the drug, the filling amount and the concentration of the drug solution 22, and the like.

The windless state refers to the case in which the wind speed is 0.5 m/s or less, including a state in which there is no wind at all. The reason for setting the wind speed to be in this range is that uneven drying rarely occurs.

In the drug solution drying step, the drug solution 22 is solidified by being dried, and is reduced compared with that in the case in which the filling with the drug solution 22 is performed. Accordingly, in the peeling-off step, the first layer 120 can be easily peeled off from the needle-like recessed portion 15 of the mold 13.

(Base Solution Filling Step)

Figure 20C:
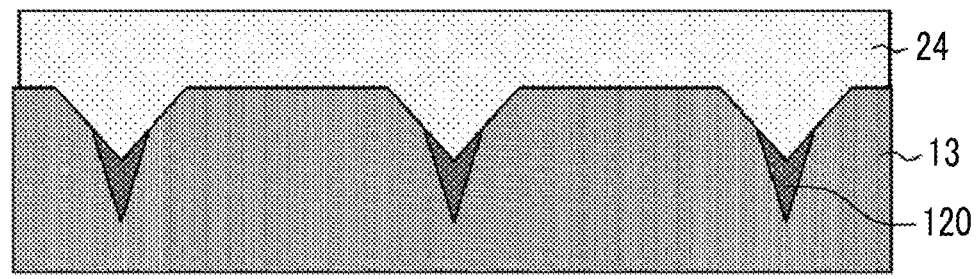
FIG. 20C is a schematic view showing a part of the step of producing a transdermal absorption sheet.

Next, as shown in FIG. 20C, a base solution 24 that is a polymer solution not containing a drug is applied to the first layer 120 containing a drug using a dispenser, and the needle-like recessed portions 15 are filled with the base solution 24. The base solution 24 in an amount larger than the spaces among the needle-like recessed portions 15 fills the needle-like recessed portions. Bar coating, spin coating, coating using a spray, or the like can be applied instead of the application using the dispenser.

In the case in which the amount of the base solution 24 is excessively large, in the following base solution drying step, the cavity portion 124 formed by drying and reduction of the base solution may extend to the frustum portion 114. Accordingly, it is preferable that the amount of the base solution 24 applied to obtain a desired cavity portion 124 is obtained in advance considering the composition, concentration, viscosity, and drying rate of the base solution 24.

By drying the base solution 24 in an appropriate amount of application, the cavity portion 124 can be formed in a dome shape, and the thickness $T_{min}$ of the thinnest part of the needle-like protruding portion 110 having the cavity portion 124 can be set to be equal to or smaller than the thickness T of the sheet portion 116 (FIGS. 3A, 3B, 7A, and 7B).

(Base Solution Drying Step)

Figure 20D:
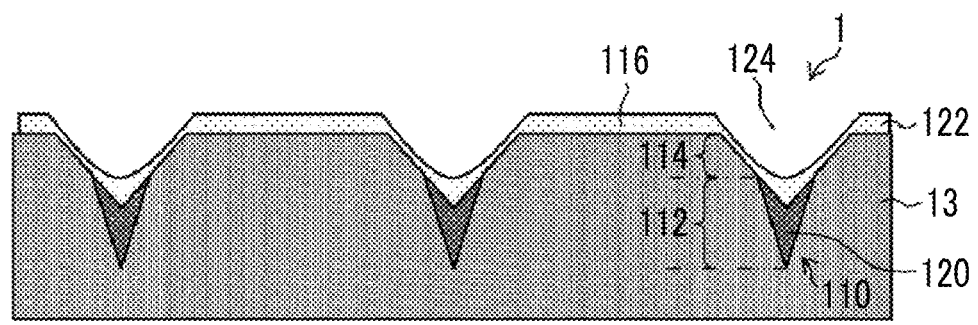
FIG. 20D is schematic view showing a part of the step of producing a transdermal absorption sheet.

Next, as shown in FIG. 20D, the second layer 122 not containing a drug is formed on the first layer 120 by drying the base solution 24 in the base solution drying step, and the needle-like protruding portions 110 each formed of the sheet portion 116, the frustum portion 114, and the needle portion 112 is formed. The cavity portion 124 extending from the sheet portion 116 to the frustum portion 114 is formed in the needle-like protruding portion 110 by drying and reducing the base solution 24 in this base solution drying step. Thus, a polymer sheet 1 (the transdermal absorption sheet 100 before the sheet is peeled off from the mold 13) is produced.

In the base solution drying step, the cavity portion 124 extending from the sheet portion 116 to the needle portion 112 through the frustum portion 114 can be formed in the needle-like protruding portion 110.

The present inventors have conducted intensive investigations on the method of forming the cavity portion 124 in the needle-like protruding portion 110. In the base solution drying step, it has been found that the cavity portion 124 is can be formed by drying and reducing the base solution 24. Particularly, it has been found that in the case in which the cavity portion 124 is formed, slow drying of the base solution 24 is suitable for forming the cavity portion 124. The slow drying can be realized by performing drying, for example, in an environment at a high humidity and a low temperature or a low wind speed.

By slowly drying the base solution 24, (1) the surface of the base solution can prevent the sheet portion 116 as a surface barrier (a phenomenon in which the surface is dried to form a film) from being wrinkled. In addition, (2) the base solution of the needle portion 112 can be prevented from being rapidly dried and reduced. Accordingly, the base solution 24 is peeled off from the surface of the mold 13 and the tip end shape of the needle-like protruding portion 110 collapses. Thus, it is possible to suppress a failure of not obtaining a good needle shape.

Particularly, it is possible to achieve formation of the cavity portion 124 and suppression of diffusion of a drug from the first layer 120 to the second layer 122 by performing drying in a low temperature environment.

In the embodiment, the base solution drying step is preferably performed in an environment at a temperature of 1° C. to 30° C. In the case in which the base solution drying step is performed in an environment at a temperature higher than 30° C., the base solution 24 dries rapidly and a surface barrier (a phenomenon in which the surface is dried to form a film) of the surface of the base solution or a needle shape defect of the needle portion may be caused.

At the tip end portion of the needle-like recessed portion 15, the first layer 120 containing a drug is present in a solidified state. In the case in which the cavity portion 124 is not present in the case of filling with the base solution 24, there is a problem in that the base solution 24 permeates through the first layer 120 and causes diffusion of the first layer 120 to the base solution 24. In the case in which the diffusion of the first layer 120 reaches the frustum portion 114 and the sheet portion 116, the drug does not permeate into the skin at the time of puncture and is wasted. In the embodiment, since the cavity portion 124 is present, as a result, the volume of the base solution present in the frustum portion 114 and/or the needle portion 112 is reduced and the drug diffused before drying is collected at the tip ends of the needle-like recessed portions 15 along the shape of the cavity portion 124. Further, since a path of the base solution 24 in which the first layer 120 diffuses can be significantly reduced in the process of drying, most components of the first layer 120 is allowed to remain in the needle portion 112. Accordingly, permeation of the base solution 24 through the first layer 120 can be suppressed, and as a result, diffusion of the first layer 120 to the base solution 24 can be suppressed.

In the embodiment, the temperature and the relative humidity preferably refers to the following environment. At a temperature of higher than 20° C. and 30° C. or lower, the relative humidity is preferably 40% RH to 80% RH. At a temperature of higher than 10° C. and 20° C. or lower, the relative humidity is preferably 35% RH to 80% RH. At a temperature of 1° C. or higher and 10° C. or lower, the relative humidity is preferably 30% RH to 80% RH. In addition, the wind speed in the case of performing drying is preferably 0 m/s to 5 m/s.

In order to form the cavity portion 124, it is necessary to make the base solution 24 flow in the drying process. It is necessary to adjust the moisture content of the surface layer of the base solution 24 to make the base solution flow. In general, the equilibrium moisture content of a substance increases as the surrounding water vapor pressure increases at a fixed temperature and as the temperature increases at a fixed water vapor pressure, the equilibrium moisture content decreases. On the other hand, since the evaporation speed of moisture becomes low at a low temperature, diffusion of moisture in the base solution 24 becomes dominant, and thus the base solution 24 flows even at a low equilibrium moisture content. As a result of intensive investigations in consideration of the above-mentioned findings, the present inventors have found that the cavity portion 124 can be formed by controlling the environment in the above condition range. The drying time changes in accordance with the amount, composition, and concentration of the base solution, the surrounding temperature and humidity, the presence of wind, and the like.

In order to provide a desired temperature and humidity environment, for example, the base solution drying step is preferably performed in a constant-temperature chamber or a constant-temperature tank having a temperature and humidity adjusting function.

In the base solution drying step, the volume of the base solution 24 is reduced by drying. Close attachment of the base solution 24 to the mold 13 during the drying leads to a reduction in volume in the film thickness direction of the sheet, and thus the film thickness is reduced. The cavity portion 124 can be formed in the frustum portion 114 and the needle portion 112 by using this phenomenon.

A low temperature environment allows the temperature of the entire base solution drying step to be decreased. However, the present inventors have found that the cavity portion 124 can be formed in the needle-like protruding portion 110 simply by cooling at least the mold 13. The cooling temperature of the mold 13 is appropriately set in accordance with the amount, composition, and concentration of the base solution, the surrounding temperature and humidity, the presence of wind, and the like, but the cooling temperature is preferably 1° C. to 20° C. and more preferably 1° C. to 15° C. The cooling temperature of the mold 13 can be obtained by directly measuring the temperature of the mold 13.

In order to perform the base solution drying step in an environment at a temperature of 1° C. or higher and 20° C. or lower, for example, the base solution drying step may be performed in a constant-temperature chamber or a constant-temperature tank.

In addition, it is possible to locally cool only the mold 13 in which the base solution 24 is retained in a liquid state by using, for example, a chiller, a Peltier element, or the like in the base solution drying step.

According to the method of producing a transdermal absorption sheet of the embodiment, it is possible to stably form the cavity portion 124. In addition, it is possible to suppress a surface barrier of the surface of the base solution and a needle shape defect of the needle portion 112 occurring in the base solution drying step and caused by rapid drying. Further, the diffusion of the first layer 120 containing a drug to the second layer 122 not containing a drug can be suppressed due to the presence of the cavity portion 124.

In addition, the cavity portion 124 preferably remains in the second layer 122. The cavity portion preferably remains in the second layer since the first layer 120 containing a drug can be held at the tip end portion of the needle-like recessed portion 15.

As the method of forming the cavity portion 124, the case the cavity portion is formed in the base solution drying step has been described but the method is not particularly limited. For example, as other methods for forming the cavity portion 124, (1) a method of performing drying in a state in which a form is applied from the opening side of the needle-like recessed portions 15 of the mold 13 according to the shape of the cavity portion 124, (2) a method of forming the cavity portion 124 by cutting the frustum portion 114 of the needle-like protruding portion 110 from the sheet portion 116 side after drying, and the like may be used.

In the case in which the base solution 24 is peeled off from the mold 13 during drying, the polymer sheet 1 shrinks in the plane direction and thus the polymer sheet may be deformed or curled. In addition, in the case in which the polymer sheet 1 is peeled off from the mold 13 in a state in which the base solution 24 in the needle-like recessed portion 15 is not sufficiently dried, a defect that the shape of the needle-like protruding portion of the polymer sheet 1 is broken or bent is easily generated. Thus, it is preferable that the polymer sheet 1 is not peeled off from the mold 13 during drying. In addition, in order to suppress curling, a layer which shrinks to the same degree as the surface with the needle-like protruding portion may be formed on the back surface of the polymer sheet 1 (a surface opposite to the surface on which the needle-like protruding portion is formed). For example, a layer is formed so as to have a film thickness at which the effect of suppressing curling has been confirmed in advance by applying the same polymer solution as the surface side (first layer 120) to the back surface side (to the second layer 122).

(Peeling-Off Step)

Figure 21:
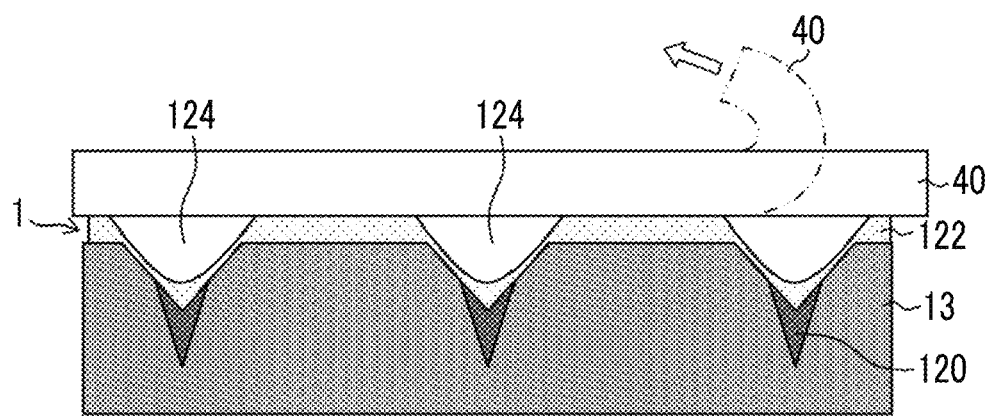
FIG. 21 is an illustration showing a peeling-off step.
Figure 22:
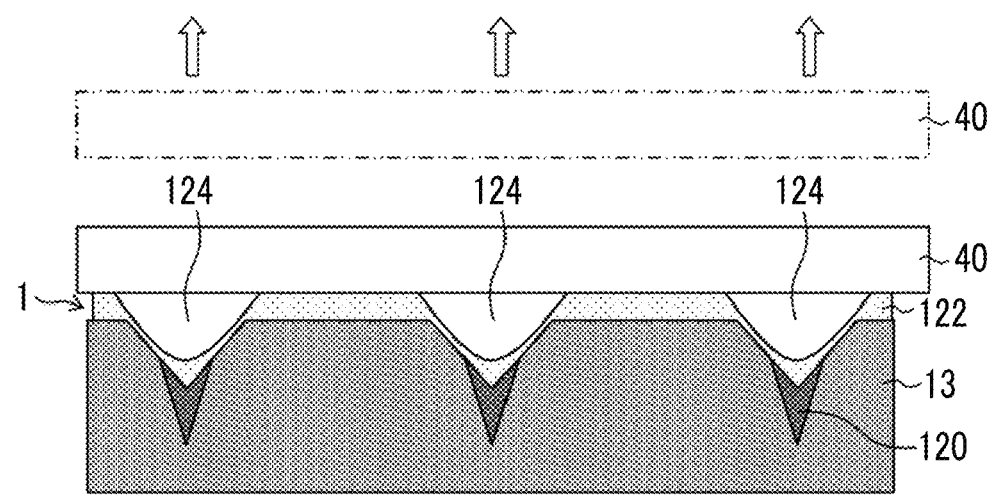
FIG. 22 is an illustration showing another peeling-off step.

The method of peeling off the polymer sheet 1 from the mold 13 is not limited. It is desirable that the needle-like protruding portion is not bent or broken during peeling-off. Specifically, as shown in FIG. 21, a sheet-like base material 40 in which an adhesive layer having adhesive properties is formed is attached to the polymer sheet 1, and then the base material 40 can be peeled off to be turned over from an end portion. However, in this method, the needle-like protruding portion may be bent. Therefore, a method in which a sucker (not shown) is installed on the back surface of the polymer sheet 1 and it is possible to vertically lift the polymer sheet while sucking the polymer sheet by air as shown in FIG. 22 can be applied. A transdermal absorption sheet 100 is produced by peeling off the polymer sheet 1 from the mold 13.

Usually, in the case in which a structure as a needle-like protruding portion having a high aspect ratio is peeled off from the mold 13 as in this embodiment, a strong stress is applied to the needle-like protruding portion due to a large contact area therebetween. In the case in which the microneedle that is the needle-like protruding portion is broken and thus remains in the needle-like recessed portion 15 without being peeled off from the mold 13, a transdermal absorption sheet to be produced has defects. In this embodiment, the mold 13 is preferably made of a material that is very easily peelable. In addition, the mold 13 is made of a soft material having, high elasticity, and thus the stress that is applied to the microneedle during peeling-off can be relaxed.

(Deaeration Step)

The drug solution 22 and/or the base solution 24 is/are preferably subjected to deaeration before the drug solution filling step and/or before the base solution filling step. Through deaeration, the air bubbles contained in the drug solution 22 and the base solution 24 can be removed before the filling of the needle-like recessed portion 15 of the mold 13. For example, in the deaeration step, air bubbles having a diameter of 100 μm to several millimeters are removed. By subjecting at least one of the drug solution 22 or the base solution 24 to deaeration, dissolution of the air bubbles in the polymer solution can be promoted.

Examples of the deaeration method include (1) a method of exposing the drug solution 22 under a reduced pressure environment for 1 to 15 minutes, (2) a method of subjecting a container storing the drug solution 22 to ultrasonic vibration for 5 to 10 minutes, (3) a method of applying ultrasonic waves while exposing the drug solution 22 under a reduced pressure environment, and (4) a method of substituting the dissolved gas with helium by sending a helium gas into the drug solution 22. Any of the deaeration methods (1) to (4) also can be applied to the base solution 24.

EXAMPLES

Hereinafter, the present invention will be described in more detail using examples of the present invention. The materials, amounts, ratios, treatment contents, treatment procedures, and the like shown in the following examples can be appropriately changed without departing from the gist of the present invention. Therefore, the scope of the present invention should not be interpreted in a limited manner based on the specific examples illustrated below.

Example 1

(Production of Mold)

Figure 23A:
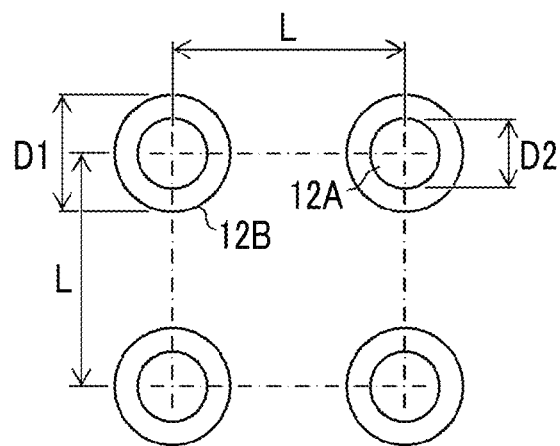
FIG. 23A is a plan view showing an original plate.
Figure 23B:
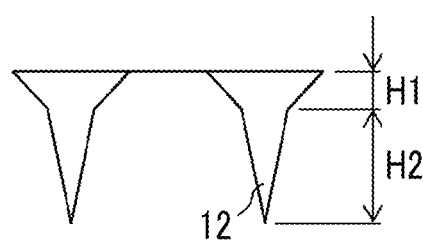
FIG. 23B is a side view showing the original plate.

An original plate 11 was produced by subjecting protruding portions 12 each with a needle-like structure to grinding at a pitch L of 1,000 μm in a two-dimensional array with 10 columns and 10 rows on the surface of a smooth Ni plate having one side of 40 mm. As shown in FIGS. 23A and 23B, each protruding portion 12 with a needle-like structure includes a truncated cone 12A with a circular bottom surface having a diameter D1 of 500 μm and a height H1 of 150 μm, and a cone 12B formed on the truncated cone 12A and having a circular bottom surface having a diameter D2 of 300 μm and a height H2 of 500 μm. On the original plate 11, a film with a thickness of 0.6 mm was formed using a silicone rubber (SILASTIC (registered trademark) MDX4-4210, manufactured by Dow Corning Corporation) as a material. The film was thermally cured in a state in which the conical tip end portions of the original plate 11 were projected by 50 μm from the film surface, and then was peeled off. Accordingly, an inverted article made of silicone rubber having through-holes having a diameter of about 30 μm was produced. The inverted article made of silicone rubber was trimmed so as to leave a planar portion with a side of 30 mm on whose central portion needle-like recessed portions were formed with two-dimensionally arranged in 10 columns and 10 rows and the obtained portion was used as a mold. The surface in which the needle-like recessed portions had wide opening portions served as a surface of the mold, and the surface having through-holes (air vent holes) having a diameter of 30 μm served as a back surface of the mold.

(Preparation of Polymer Solution Containing Drug)

Hydroxyethyl starch (manufactured by Fresenius Kabi) was dissolved in water to prepare an aqueous solution of 8%. To this aqueous solution, 2% by mass of human serum albumin (manufactured by Wako Pure Chemical Industries, Ltd.) as a drug and 0.01% by mass of EVANS BLUE dye (manufactured by Wako Pure Chemical Industries, Ltd.) were added to prepare a drug solution containing a drug.

(Preparation of Polymer Solution Not Containing Drug)

Chondroitin sulfate (manufactured by Manilla Nichiro Corporation) was dissolved in water to prepare an aqueous solution of 40% as a solution not containing a drug.

Hereinafter, the drug solution filling step, the drug solution drying step, and the base solution drying step were performed in an environment at a temperature of 10° C., and the base solution filling step was performed in an environment at a temperature of 15° C.

(Drug Solution Filling Step and Drug Solution Drying Step)

A drug solution filling apparatus is provided with a driving unit that has a X-axis driving unit and Z-axis driving unit controlling relative position coordinates of the mold and the nozzle, a liquid supply apparatus (super small amount fixed-quantity dispenser SMP-III, manufactured by Masashi Engineering, Inc.) on which the nozzle can be mounted, a suction base to which the mold is fixed, a laser displacement meter (HL-C201A, manufactured by Panasonic Corporation) that measures the surface shape of the mold, a load cell (LCX-A-500N, manufactured by Kyowa Electronic Instruments Co., Ltd.) that measures a nozzle pressing pressure, and a control system that controls the Z axis based on data of measured values of the surface shape and the pressing pressure.

A gas permeable film (POREFLON (registered trademark) FP-010, manufactured by Sumitomo Electric Industries, Ltd.) having one side of 15 mm was placed on the flat suction base, and the mold was installed thereon such that the surface thereof was positioned on the upper side. The gas permeable film and the mold were fixed to the vacuum board by pressure reduction with a suction pressure of 90 kPa gauge pressure in the back surface direction of the mold.

A stainless steel nozzle having the shape shown in FIG. 14 was prepared, and a slit-shaped opening portion having a length of 12 mm and a width of 0.2 mm was formed at the center of a lip portion having a length of 20 mm and a width of 0.2 mm. This nozzle was connected to the drug solution tank. The drug solution tank and the nozzle were filled with 3 mL of a solution containing a drug. The nozzle was adjusted such that the opening portion was parallel to the first column of a plurality of needle-like recessed portions formed in the surface of the mold. The nozzle was pressed against the mold at a pressure (pressing force) of 0.14 kgf/cm$^2$ (1.4 N/cm$^2$) at a position apart from the first column with an interval of 2 mm therebetween in a direction opposite to the second column. While being pressed, the nozzle was moved at 1 mm/sec in a direction perpendicular to a length direction of the opening portion while the Z axis was controlled such that the pressing force changed within ±0.05 kgf/cm$^2$ (0.49 N/cm$^2$). Simultaneously, the drug-containing solution was discharged from the opening portion for 10 seconds at 0.31 µL/sec by the liquid supply apparatus. The movement of the nozzle was stopped at a position apart from the tenth column of the plurality of needle-like recessed portions arranged two-dimensionally with an interval of 2 mm therebetween in a direction opposite to the ninth column, and the nozzle was separated from the mold.

The mold filled with the drug solution was put and dried in a windshield (25 cm$^3$) with an opening portion having a diameter of 5 mm. The windshield mentioned herein has a gas permeable film (POREFLON (registered trademark) FP-010, manufactured by Sumitomo Electric Industries, Ltd.) mounted on the opening portion and is structured so as not to be directly exposed to wind to provide a windless state.

(Base Solution Filling Step and Base Solution Drying Step)

A thin stainless steel plate having an opening portion with a diameter of 16 mm and having a thickness of 300 µm was prepared on the surface of the mold. The mold filled with the drug solution was fixed to the suction base by suction and the position was adjusted such that the needle-like recessed portion region was placed in the opening portion to laminate the mold and the thin stainless steel plate. The base solution was poured into the opening portion of the thin stainless steel plate. An excessive amount of the base solution was scraped off with a squeegee or round bar and the mold was cooled to 15° C. in an environment at a temperature of 23° C., a relative humidity of 50% RH, and a wind speed of 0.5 m/s and left to stand to dry the solution for 3 hours.

(Peeling-Off Step)

The polymer sheet was peeled off from the mold so as to be turned over from the end portion. On the sheet portion, a transdermal absorption sheet in which needle-like protruding portions each including a first layer containing a drug in which the human serum albumin was unevenly distributed at the tip end and a second layer not containing a drug, and formed of a frustum portion and a needle portion were arranged was produced.

After the peeling-off, the transdermal absorption sheet was observed using a microscope (VHX-600 manufactured by Keyence Corporation). A dome-shaped cavity portion extending from the sheet portion was formed in the frustum portion of the needle-like protruding portion and the thickness of the thinnest part of the needle-like protruding portion having the cavity portion was equal to or smaller than the thickness of the sheet portion.

Example 2

A transdermal absorption sheet in which needle-like protruding portions were arranged was produced under the same conditions as in Example 1 except that in the base solution filling step, a thin stainless steel plate having an opening portion with a diameter of 16 mm and having a thickness of 200 µm was used.

After the peeling-off, the transdermal absorption sheet was observed using a microscope (VHX-600 manufactured by Keyence Corporation). A dome-shaped cavity portion extending from the sheet portion was formed in the needle portion of the needle-like protruding portion and the thickness of the thinnest part of the needle-like protruding portion having the cavity portion was equal to or smaller than the thickness of the sheet portion.

Comparative Example

A transdermal absorption sheet in which needle-like protruding portions were arranged was produced under the same conditions as in Example 1 except that in the base solution filling step, a thin stainless steel plate having an opening portion with a diameter of 16 mm and having a thickness of 1,000 µm was used and the mold was left to stand and dry for 12 hours without cooling the mold in an environment at a temperature of 23° C., a relative humidity of 50% RH, and a wind speed of 0.5 m/s.

After the peeling-off, the transdermal absorption sheet was observed using a microscope (VHX-600 manufactured by Keyence Corporation). It was confirmed that a transdermal absorption sheet formed of needles not having a cavity portion was formed.

(Evaluation Results)

Regarding the dissolution rate, needle-like protruding portions were used to puncture a rat skin. The lengths of the needle-like protruding portions remaining in the skin after 3 minutes from the puncture were compared for evaluation. In the transdermal absorption sheet with needle-like protruding portions having a cavity portion, the dissolution rate was high compared to the transdermal absorption sheet not having a cavity portion. That is, it is possible to understand that the dissolution rate can be controlled by providing a cavity portion in the needle-like protruding portion.

In addition, regarding diffusion of the drug, a transdermal absorption sheet was produced using a polymer solution containing a drug to which 0.01% of EVANS BLUE was added, and dye distribution of a side surface was observed using a microscope to evaluate a dye diffusion distance from the tip end of the needle to the second layer.

In the transdermal absorption sheet having a cavity portion, the diffusion distance was short compared to the transdermal absorption sheet not having a cavity portion. That is, it is possible to understand that the diffusion distance from the first layer to the second layer can be shorted and diffusion of the drug of the first layer to the second layer can be suppressed by providing a cavity portion in the needle-like protruding portion.

EXPLANATION OF REFERENCES

1: polymer sheet
11: original plate
12: protruding portion
13: mold
14: frame
15: needle-like recessed portion
15A: inlet portion
15B: tip end recessed portion
15C: through-hole
17: substrate
18: mold complex
19: gas permeable sheet
20: base
22: drug solution
24: base solution
30: liquid feed tank
32: pipe
34: nozzle
34A: lip portion
34B: opening portion
34C: inclined surface
40: base material
36: liquid supply apparatus
48: drug solution filling apparatus
50: Z-axis driving unit
52: suction base
54: X-axis driving unit
56: stand
58: control system
60: laser displacement meter
100: transdermal absorption sheet
110: needle-like protruding portion
112: needle portion
112A: tapered needle-like portion
112B: body portion
114: frustum portion
116: sheet portion
120: first layer
122: second layer
124: cavity portion
126: opening
130: skin

What is claimed is:

1. A transdermal absorption sheet comprising:
   a sheet portion; and
   a plurality of needle-shaped protruding portions which are arranged on the sheet portion and formed of frustum portions and needle portions, and in each of which a wide bottom surface of the frustum portion is connected to the sheet portion and a narrow bottom surface of the frustum portion is connected to a wide bottom surface of the needle portion,
   wherein each of the plurality of needle portions includes a first layer containing a drug or a cosmetic component and a second layer not containing the drug and the cosmetic component,
   at least one of the plurality of needle-shaped protruding portions has a cavity portion extending from the sheet portion to the frustum portion, and
   the cavity portion is entirely or partially formed in a dome shape.

2. The transdermal absorption sheet according to claim 1, wherein at least one of the plurality of needle-shaped protruding portions has a cavity portion extending from the sheet portion to the needle portion through the frustum portion.

3. The transdermal absorption sheet according to claim 1, wherein a radius of curvature that defines the dome shape is 10 µm or more.

4. The transdermal absorption sheet according to claim 1, wherein a thickness of the thinnest part of the needle-shaped protruding portion having the cavity portion is equal to or less than a thickness of the sheet portion.

5. The transdermal absorption sheet according to claim 4, wherein the thickness of the thinnest part is in a range of 100 to 500 µm.

6. The transdermal absorption sheet according to claim 1, wherein the cavity portion remains in the second layer.

7. The transdermal absorption sheet according to claim 1, wherein the drug is at least one of peptide, protein, nucleic acid, polysaccharide, a vaccine, or a medical compound.

8. A method of producing a transdermal absorption sheet comprising, in this order:
   a solution filling step of filling needle-shaped recessed portions of a mold having the needle-shaped recessed portions arranged two-dimensionally with a solution which is a polymer solution containing a drug or a cosmetic component;
   a solution drying step of drying the solution filling the needle-shaped recessed portions to form a first layer containing the drug or the cosmetic component;
   a base solution filling step of filling the needle-shaped recessed portions with a base solution that is a polymer solution not containing the drug and the cosmetic component on the first layer;
   a base solution drying step of drying the base solution to form a second layer not containing the drug and the cosmetic component on the first layer and forming needle-shaped portions formed of frustum portions and needle portions and a sheet portion; and
   a peeling-off step of peeling off the sheet portion and the needle-shaped protruding portions from the mold,
   wherein in the base solution drying step, a cavity portion extending from the sheet portion to the frustum portion or a cavity portion extending from the sheet portion to the needle portion through the frustum portion is formed in the needle-shaped protruding portion by drying and reducing the base solution.

9. The method of producing a transdermal absorption sheet according to claim 8,
   wherein the base solution drying step includes drying the base solution while cooling the mold.

10. The method of producing a transdermal absorption sheet according to claim 9,
   wherein a cooling temperature for cooling the mold is in a range of 1° C. to 20° C.

* * * * *